United States Patent
Sohn et al.

(10) Patent No.: US 9,719,112 B2
(45) Date of Patent: Aug. 1, 2017

(54) MUTANT BETA-GLUCOSIDASES HAVING ENHANCED ACTIVITY AND A METHOD FOR PRODUCING BIOETHANOL USING THE SAME

(75) Inventors: Jung Hoon Sohn, Daejeon (KR); Hyun Jin Kim, Daejeon (KR); Chul Ho Kim, Daejeon (KR); Ji Hun Seomoon, Daejeon (KR); Bong Hyun Sung, Daejeon (KR); Kwang Mook Lim, Daejeon (KR); Mi Jin Kim, Daejeon (KR); Jong Hyun Kim, Daejeon (KR)

(73) Assignee: KOREA RESEARCH INSITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 794 days.

(21) Appl. No.: 14/111,721

(22) PCT Filed: Apr. 13, 2012

(86) PCT No.: PCT/KR2012/002846
§ 371 (c)(1),
(2), (4) Date: Jun. 22, 2015

(87) PCT Pub. No.: WO2012/141547
PCT Pub. Date: Oct. 18, 2012

(65) Prior Publication Data
US 2015/0299733 A1    Oct. 22, 2015

(30) Foreign Application Priority Data

Apr. 13, 2011   (KR) .................. 10-2011-0034162

(51) Int. Cl.
*C12P 7/06* (2006.01)
*C12P 7/08* (2006.01)
*C12P 7/10* (2006.01)
*C12N 9/42* (2006.01)

(52) U.S. Cl.
CPC .............. *C12P 7/06* (2013.01); *C12N 9/2445* (2013.01); *C12Y 302/01021* (2013.01); *Y02E 50/17* (2013.01)

(58) Field of Classification Search
None
See application file for complete search history.

(56) References Cited

FOREIGN PATENT DOCUMENTS

| | | |
|---|---|---|
| KR | 1006973100000 | 3/2007 |
| KR | 1020100091289 | 8/2010 |
| KR | 1020100131208 | 12/2010 |
| KR | 1020110007981 | 1/2011 |
| WO | 2008155665 A2 | 12/2008 |

OTHER PUBLICATIONS

Dawes et al., Biochim. Biophys. Acta vol. 22, p. 253, 1956.*
Choi et al., Appl. Microbiol. Biotechnol. 64:625-635, 2004.*
Liu et al. 'Fast Identification of Thermostable Beta-Glucosidase Mutants on Cellobiose by a Novel Combinatorial Selection/Screening Approach'. Biotechnology & Bioengineering. 2009, vol. 103, pp. 1087-1094.

* cited by examiner

*Primary Examiner* — David J Steadman
(74) *Attorney, Agent, or Firm* — Lathrop & Gage LLP; Brian C. Trinque

(57) ABSTRACT

The present invention relates to beta-glucosidase that is mutated to have enhanced activity, and a method for producing bioethanol using the same. More particularly, the present invention relates to a polynucleotide encoding beta-glucosidase that is mutated to have enhanced activity, beta-glucosidase expressed from the polynucleotide, an expression vector including the polynucleotide, a transformant that is transformed with the expression vector, a method for producing the mutated beta-glucosidase using the transformant, and a method for producing bioethanol using the transformant. The mutant beta-glucosidase of the present invention increases production of glucose much more than the conventional beta-glucosidase, and thus it can be widely used for economic production of bioethanol.

15 Claims, 17 Drawing Sheets

YP-CB 2 day culture          YP-CB-Antimycin 6 day

FIG. 9b

|  | Beta-glucosidase activity (U/ml) |
|---|---|
| Control | 1378.6 |
| 1 | 1469.8 |
| 2 | 1458.4 |
| 3 | 1402.5 |
| 4 | 1413.5 |
| 5 | 1574.2 |
| 6 | 1545.6 |
| 7 | 1788.9 |
| 8 | 1678.2 |
| 9 | 1477.6 |
| 10 | 1793.8 |
| 11 | 1635.2 |
| 12 | 1994.5 |
| 13 | 1563.6 |
| 14 | 1874.1 |
| 15 | 1423.3 |
| 16 | 1310.3 |
| 17 | 1369.8 |

SEQUENCE LISTING

<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
catgaattca aaatgttgat gatagtacag                                    30

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ctgccgagac ctttgcattg c                                             21

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ctcgccttag ataaaagagt cccaattcaa aactatac                           38

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
cactccgttc aagtcgactt aaatagtaaa caggacag                           38

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
ggccgcctcg gcctctgctg gcctcgcctt agataaaaga                         40

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
gtcattatta aatatatata tatatatatt gtcactccgt tcaagtcgac              50

```
<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcgtccatcc aaaaaaaaag taagaatttt tgaaaattca agaattc                    47

<210> SEQ ID NO 8
<211> LENGTH: 2580
<212> TYPE: DNA
<213> ORGANISM: Artificial Sequence
<220> FEATURE:
<223> OTHER INFORMATION: Description of Artificial Sequence: Synthetic
      SfBGL1 polynucleotide

<400> SEQUENCE: 8
gtcccaattc aaaactatac ccagtctcca tcccaaggcg atgagagctc ccaatgggtg      60
agcccgcatt attatccaac tccacaaggt ggtaggctcc aagacgtctg gcaagaagca     120
tatgctagag caaaagccat cgttggccag atgactattg ttgaaaaggt caatttgacc     180
accggtaccg gttggcaatt agatccatgt gttggtaata ccggttctgt tccaagattt     240
ggcatcccaa acctttgcct acaagatggg ccattgggtg tccgattcgc tgactttgtt     300
acaggctatc catccggtct tgccaccggt gcaacgttca ataaggattt gttccttcaa     360
agaggtcaag ctcttggcca cgagttcaac agcaaaggtg tacatattgc attgggccct     420
gctgttggcc cacttggtgt caaagccaga ggtggcagaa atttcgaggc ctttggttcc     480
gacccatatc tccaaggtat tgctgctgct gcaaccatca aggtctccaa agagaataat     540
gttatggctt gtgtcaagca ctttattggt aacgaacaag aaaagtacag acaaccagat     600
gacatgaatc ctgccaccaa ccaaactact aaagaagcta agtgctaa tattccagac      660 agagccatgc atgagttgta cttgtggcca tttgcggatt cggttcgggc aggtgttggt     720
tctgttatgt gctcttataa cagagtcaac aacacttacg cttgcgaaaa ctcttacatg     780
atgaaccact tgcttaaaga agaattgggt tttcaaggct tgttgtttc ggactggggt     840 gcacaattaa gtggggttta tagcgctatc tcgggcttag atatgtctat gcctggtgaa     900
gtgtatgggg gatggaacac cggcacgtct ttctggggtc aaaacttgac gaaagctatt     960
tacaatgaga ctgtcccgat tgaaagatta gatgatatgg caaccaggat cttggctgct    1020
ttgtatgcta ccaatagttt cccaacagaa gatcaccttc caattttttc ttcatggaca   1080
acgaaagaat atggcaataa atattatgct gacaacacta ccgagattgt caaagtcaac   1140
tacaatgtgg acccatcaaa tgactttacg gaggacacag ctttgaaggt tgctgaggaa   1200
tctattgtgc ttttaaaaaa tgaaacaac actttgccaa tttctcccga aaaggctaaa    1260
agattactat tgtcgggtat tgctgcaggc cctgatccga taggttatca gtgtgaagat   1320
caatcttgca caaatggcgc tttgtttcaa ggttgggggtt ctggcagtgt tggttctcca   1380
aaatatcaag tcactccatt tgaggaaatt tcttatcttg caagaaaaag caagatgcaa   1440
tttgattata ttcgggagtc ttacgactta gctcaagtta ctaaagtagc ttccgatgct    1500
catttgtcta tagttgttgt ctctgctgca agcggtgagg ttatataac cgttgacggt     1560 aaccaaggtg acagaaaaaa tctcactttg tggaacaacg gtgataaatt gattgaaaca    1620
```

| | | | | |
|---|---|---|---|---|
| gtcgctgaaa | actgtgccaa | tactgttgtt | gttgttactt | ctactggtca aattaatttt | 1680 |
| gaaggctttg | ctgatcaccc | aaatgttacc | gcaattgtct | gggctggccc attaggtgac | 1740 |
| agatccggga | ctgctatcgc | caatattctt | tttggtaaag | cgaacccatc aggtcatctt | 1800 |
| ccattcacta | tcgctaagac | tgacgatgat | tacattccaa | ttgaaatcta cagtccatcg | 1860 |
| agtggtgagc | ctgaagacaa | ccacttggtt | gaaaatgact | tgcttgttga ctatagatat | 1920 |
| tttgaagaga | agaatattga | gccaagatac | gctatttggct | atggcttgtc ttacaatgag | 1980 |
| tataaagtta | gcaatgcaaa | ggtctcggca | gccaaaaaag | ttgatgagga gttgcctgaa | 2040 |
| ccagctacct | acttatcgga | gtttagctat | caaaatgcaa | aaggcagcaa aaatccaagt | 2100 |
| gatgcttttg | ctccagcaga | tttaaacaga | gttaatgagt | acctttatcc atatttagat | 2160 |
| agcaatgtta | ccttgaaaga | cggaaactat | gagtatcctg | atggctacag cactgagcaa | 2220 |
| agaacaacac | ctatccaacc | tgggggcggc | ttgggaggca | acgatgcttt gtgggaggtc | 2280 |
| gcttataaag | ttgaagtgga | cgttcaaaac | ttgggtaact | ccactgataa gtttgttcca | 2340 |
| cagttgtatt | tgaaacaccc | tgaagatggc | aagtttgaaa | ccccggttca attgagaggg | 2400 |
| ttcgaaaagg | ttgagttgtc | cccgggtgag | aagaagacag | ttgagtttga gcttttgaga | 2460 |
| agagatctta | gtgtgtggga | taccatcaga | caatcctgga | tcgttgaatc tggtacttat | 2520 |
| gaggccttaa | ttggtgttgc | tgttaataat | atcaagacat | ctgtcctgtt tactatttaa | 2580 |

<210> SEQ ID NO 9
<211> LENGTH: 2580
<212> TYPE: DNA
<213> ORGANISM: Artificial Sequence
<220> FEATURE:
<223> OTHER INFORMATION: Description of Artificial Sequence: Synthetic
    mutated SfBGL1 polynucleotide

<400> SEQUENCE: 9

| | | | | |
|---|---|---|---|---|
| gtcccaattc | aaaactatac | ccagtctcca | tcccaaggcg | atgagagctc ccaatgggtg | 60 |
| agcccgcatt | attatccaac | tccacaaggt | ggtaggctcc | aagacgtctg gcaggaagca | 120 |
| tatgctagag | caaaagccat | cgttggccag | atgactattg | ttgaaaaggt caatttgacc | 180 |
| accggtaccg | gttggcaatt | agatccatgt | gttggtaata | ccggttctgt tccaagattt | 240 |
| ggcatcccaa | acctttgcct | acaagatggg | ccattgggtg | tccgattcgc tgactttgtt | 300 |
| acaggctatc | catccggtct | tgccaccggt | gcaacgttca | taaggatttg gttccttcaa | 360 |
| agaggtcaag | ctcttggcca | cgagttcaac | agcaaaggtg | tacatattgc attgggccct | 420 |
| gctgttggcc | cacttggtgt | caaagccaga | ggtggcagaa | atttcgaggc ctttggttcc | 480 |
| gacccatatc | tccaaggtat | tgctgctgct | gcaaccatca | aggtctccaa agagaataat | 540 |
| gttatggctt | gtgtcaagca | ctttattggt | aacgaacaag | aaaagtacag acaaccagat | 600 |
| gacatgaatc | ctgccaccaa | ccaaactact | aaagaagcta | agtgctaa tattccagac | 660 |
| agagccatgc | atgagttgta | cttgtggcca | tttgcggatt | cggttcgggc aggtgttggt | 720 |
| tctgttatgt | gctcttataa | cagagtcaac | aacacttacg | cttgcgaaaa ctcttacatg | 780 |
| atgaaccact | tgcttaaaga | agaattgggt | tttcaaggct | tgttgtttc ggactggggt | 840 |
| gcacaattaa | gtgggtttta | tagcgctatc | tcgggcttag | atatgtctat gcctggtgaa | 900 |
| gtgtatgggg | gatggaacac | cggcacgtct | ttctgggtc | aaaacttgac gaaagctatt | 960 |
| tacaatgaga | ctgtcccgat | tgaaagatta | atgatatgg | caaccaggat cttggctgct | 1020 |
| ttgtatgcta | ccaatagttt | cccaacagaa | gatcaccttc | caaattttc ttcatggaca | 1080 |

```
acgaaagaat atggcaataa atattatgct gacaacacta ccgagattgt caaagtcaac    1140
tacaatgtgg acccatcaaa tgactttacg gaggacacag cttttgaaggt tgctgaggaa    1200 tctattgtgc ttttaaaaaa tgaaaacaac actttgccaa tttctcccga aaaggctaaa    1260
agattactat tgtcgggtat tgctgcaggc cctgatccga taggttatca gtgtgaagat    1320
caatcttgca caaatggcgc tttgtttcaa ggttggggtt ctggcagtgt tggttcccca    1380
aaatatcaag tcactccatt tgaggaaatt tcttatcttg caagaaaaag caagatgcaa    1440
tttgattata ttcgggagtc ttacgactta gctcaagtta ctaaagtagc ttccgatgct    1500
catttgtcta tagttgttgt ctctgcagca agcggtgagg ttatataac  cgttgacggt    1560 aaccaaggtg acagaaaaaa tctcactttg tggaacaacg gtgataaatt gattgaaaca    1620
gtcgctgaaa actgtgccaa tactgttgtt gttgttactt ctactggtca aattaatttt    1680
gaaggctttg ctgatcaccc aaatgttacc gcaattgtct gggctggccc attaggtgac    1740
agatccggga ctgctatcgc caatattctt tttggtaaag cgaacccatc aggtcatctt    1800
ccattcacta tcgctaagac tgacgatgat tacattccaa ttgaaatcta cagtccatcg    1860
agtggtgagc ctgaagacaa ccacttggtt gaaaatgact tgcttgttga ctatagatat    1920
tttgaagaga agaatattga gccaagatac gcatttggct atggcttgtc ttacaatgag    1980
tataaagtta gcaatgcaaa ggtctcggca gccaaaaaag ttgatgagga gttgcctgaa    2040
ccagctacct actatcgga gtttagctat caaaatgcaa aaggcagcaa aaatccaagt    2100
gatgcttttg ctccagcaga tttaaacaga gttaatgagt accttttatcc atatttagat    2160 agcaatgtta ccttgaaaga cggaaactat gagtatcctg atggctacag cactgagcaa    2220
agaacaacac ctatccaacc tggggggcggc ctgggaggca acgatgcttt gtgggaggtc    2280
gcttataaag ttgaagtgga cgttcaaaac ttgggtaact ccactgataa gtttgttcca    2340
cagttgtatt tgaaacaccc tgaagatggc aagtttgaaa ccccggttca attgagaggg    2400
ttcgaaaagg ttgagttgtc cccgggtgag aagaagacag ttgagtttga gcttttgaga    2460
agagatctta gtgtgtggga taccatcaga caatcctgga tcgttgaatc tggtacttat    2520
gaggccttaa ttggtgttgc tgttaataat atcaagacat ctgtcctgtt tactatttaa    2580
```

<210> SEQ ID NO 10
<211> LENGTH: 859
<212> TYPE: PRT
<213> ORGANISM: Artificial Sequence
<220> FEATURE:
<223> OTHER INFORMATION: Description of Artificial Sequence: Synthetic
    SfBGL1 polypeptide

<400> SEQUENCE: 10

```
Val Pro Ile Gln Asn Tyr Thr Gln Ser Pro Ser Gln Gly Asp Glu Ser
1               5                   10                  15

Ser Gln Trp Val Ser Pro His Tyr Tyr Pro Thr Pro Gln Gly Gly Arg
            20                  25                  30

Leu Gln Asp Val Trp Gln Glu Ala Tyr Ala Arg Ala Lys Ala Ile Val
        35                  40                  45

Gly Gln Met Thr Ile Val Glu Lys Val Asn Leu Thr Thr Gly Thr Gly
    50                  55                  60

Trp Gln Leu Asp Pro Cys Val Gly Asn Thr Gly Ser Val Pro Arg Phe
65                  70                  75                  80

Gly Ile Pro Asn Leu Cys Leu Gln Asp Gly Pro Leu Gly Val Arg Phe
                85                  90                  95
```

```
Ala Asp Phe Val Thr Gly Tyr Pro Ser Gly Leu Ala Thr Gly Ala Thr
            100                 105                 110

Phe Asn Lys Asp Leu Phe Leu Gln Arg Gly Gln Ala Leu Gly His Glu
        115                 120                 125

Phe Asn Ser Lys Gly Val His Ile Ala Leu Gly Pro Ala Val Gly Pro
        130                 135                 140

Leu Gly Val Lys Ala Arg Gly Gly Arg Asn Phe Glu Ala Phe Gly Ser
145                 150                 155                 160

Asp Pro Tyr Leu Gln Gly Ile Ala Ala Ala Thr Ile Lys Gly Leu
                165                 170                 175

Gln Glu Asn Asn Val Met Ala Cys Val Lys His Phe Ile Gly Asn Glu
            180                 185                 190

Gln Glu Lys Tyr Arg Gln Pro Asp Asp Met Asn Pro Ala Thr Asn Gln
        195                 200                 205

Thr Thr Lys Glu Ala Ile Ser Ala Asn Ile Pro Asp Arg Ala Met His
        210                 215                 220

Glu Leu Tyr Leu Trp Pro Phe Ala Asp Ser Val Arg Ala Gly Val Gly
225                 230                 235                 240

Ser Val Met Cys Ser Tyr Asn Arg Val Asn Asn Thr Tyr Ala Cys Glu
                245                 250                 255

Asn Ser Tyr Met Met Asn His Leu Leu Lys Glu Glu Leu Gly Phe Gln
            260                 265                 270

Gly Phe Val Val Ser Asp Trp Gly Ala Gln Leu Ser Gly Val Tyr Ser
                275                 280                 285

Ala Ile Ser Gly Leu Asp Met Ser Met Pro Gly Glu Val Tyr Gly Gly
        290                 295                 300

Trp Asn Thr Gly Thr Ser Phe Trp Gly Gln Asn Leu Thr Lys Ala Ile
305                 310                 315                 320

Tyr Asn Glu Thr Val Pro Ile Glu Arg Leu Asp Asp Met Ala Thr Arg
                325                 330                 335

Ile Leu Ala Ala Leu Tyr Ala Thr Asn Ser Phe Pro Thr Glu Asp His
            340                 345                 350

Leu Pro Asn Phe Ser Ser Trp Thr Thr Lys Glu Tyr Gly Asn Lys Tyr
        355                 360                 365

Tyr Ala Asp Asn Thr Thr Glu Ile Val Lys Val Asn Tyr Asn Val Asp
370                 375                 380

Pro Ser Asn Asp Phe Thr Glu Asp Thr Ala Leu Lys Val Ala Glu Glu
385                 390                 395                 400

Ser Ile Val Leu Leu Lys Asn Glu Asn Asn Thr Leu Pro Ile Ser Pro
                405                 410                 415

Glu Lys Ala Lys Arg Leu Leu Leu Ser Gly Ile Ala Ala Gly Pro Asp
            420                 425                 430

Pro Ile Gly Tyr Gln Cys Glu Asp Gln Ser Cys Thr Asn Gly Ala Leu
        435                 440                 445

Phe Gln Gly Trp Gly Ser Gly Ser Val Gly Ser Pro Lys Tyr Gln Val
        450                 455                 460

Thr Pro Phe Glu Glu Ile Ser Tyr Leu Ala Arg Lys Ser Lys Met Gln
465                 470                 475                 480

Phe Asp Tyr Ile Arg Glu Ser Tyr Asp Leu Ala Gln Val Thr Lys Val
                485                 490                 495

Ala Ser Asp Ala His Leu Ser Ile Val Val Ser Ala Ala Ser Gly
            500                 505                 510

Glu Gly Tyr Ile Thr Val Asp Gly Asn Gln Gly Asp Arg Lys Asn Leu
```

-continued

```
            515                 520                 525
Thr Leu Trp Asn Asn Gly Asp Lys Leu Ile Glu Thr Val Ala Glu Asn
        530                 535                 540

Cys Ala Asn Thr Val Val Val Thr Ser Thr Gly Gln Ile Asn Phe
545                 550                 555                 560

Glu Gly Phe Ala Asp His Pro Asn Val Thr Ala Ile Val Trp Ala Gly
                565                 570                 575

Pro Leu Gly Asp Arg Ser Gly Thr Ala Ile Ala Asn Ile Leu Phe Gly
            580                 585                 590

Lys Ala Asn Pro Ser Gly His Leu Pro Phe Thr Ile Ala Lys Thr Asp
                595                 600                 605

Asp Asp Tyr Ile Pro Ile Glu Ile Tyr Ser Pro Ser Ser Gly Glu Pro
            610                 615                 620

Glu Asp Asn His Leu Val Glu Asn Asp Leu Leu Val Asp Tyr Arg Tyr
625                 630                 635                 640

Phe Glu Glu Lys Asn Ile Glu Pro Arg Tyr Ala Phe Gly Tyr Gly Leu
                645                 650                 655

Ser Tyr Asn Glu Tyr Lys Val Ser Asn Ala Lys Val Ser Ala Ala Lys
            660                 665                 670

Lys Val Asp Glu Glu Leu Pro Glu Pro Ala Thr Tyr Leu Ser Glu Phe
                675                 680                 685

Ser Tyr Gln Asn Ala Lys Gly Ser Lys Asn Pro Ser Asp Ala Phe Ala
        690                 695                 700

Pro Ala Asp Leu Asn Arg Val Asn Glu Tyr Leu Tyr Pro Tyr Leu Asp
705                 710                 715                 720

Ser Asn Val Thr Leu Lys Asp Gly Asn Tyr Glu Tyr Pro Asp Gly Tyr
                725                 730                 735

Ser Thr Glu Gln Arg Thr Thr Pro Ile Gln Pro Gly Gly Leu Gly
            740                 745                 750

Gly Asn Asp Ala Leu Trp Glu Val Ala Tyr Lys Val Glu Val Asp Val
                755                 760                 765

Gln Asn Leu Gly Asn Ser Thr Asp Lys Phe Val Pro Gln Leu Tyr Leu
        770                 775                 780

Lys His Pro Glu Asp Gly Lys Phe Glu Thr Pro Val Gln Leu Arg Gly
785                 790                 795                 800

Phe Glu Lys Val Glu Leu Ser Pro Gly Glu Lys Lys Thr Val Glu Phe
                805                 810                 815

Glu Leu Leu Arg Arg Asp Leu Ser Val Trp Asp Thr Ile Arg Gln Ser
            820                 825                 830

Trp Ile Val Glu Ser Gly Thr Tyr Glu Ala Leu Ile Gly Val Ala Val
        835                 840                 845

Asn Asn Ile Lys Thr Ser Val Leu Phe Thr Ile
        850                 855

<210> SEQ ID NO 11
<211> LENGTH: 859
<212> TYPE: PRT
<213> ORGANISM: Artificial Sequence
<220> FEATURE:
<223> OTHER INFORMATION: Description of Artificial Sequence: Synthetic
      SfBGL1-10 polypeptide

<400> SEQUENCE: 11

Val Pro Ile Gln Asn Tyr Thr Gln Ser Pro Ser Gln Gly Asp Glu Ser
1               5                   10                  15
```

```
Ser Gln Trp Val Ser Pro His Tyr Tyr Pro Thr Pro Gln Gly Gly Arg
            20                  25                  30

Leu Gln Asp Val Trp Gln Glu Ala Tyr Ala Arg Ala Lys Ala Ile Val
            35                  40                  45

Gly Gln Met Thr Ile Val Glu Lys Val Asn Leu Thr Thr Gly Thr Gly
            50                  55                  60

Trp Gln Leu Asp Pro Cys Val Gly Asn Thr Gly Ser Val Pro Arg Phe
65                  70                  75                  80

Gly Ile Pro Asn Leu Cys Leu Gln Asp Gly Pro Leu Gly Val Arg Phe
                85                  90                  95

Ala Asp Phe Val Thr Gly Tyr Pro Ser Gly Leu Ala Thr Gly Ala Thr
                100                 105                 110

Phe Asn Lys Asp Leu Phe Leu Gln Arg Gly Gln Ala Leu Gly His Glu
                115                 120                 125

Phe Asn Ser Lys Gly Val His Ile Ala Leu Gly Pro Ala Val Gly Pro
                130                 135                 140

Leu Gly Val Lys Ala Arg Gly Gly Arg Asn Phe Glu Ala Phe Gly Ser
145                 150                 155                 160

Asp Pro Tyr Leu Gln Gly Ile Ala Ala Ala Thr Ile Lys Gly Leu
                165                 170                 175

Gln Glu Asn Asn Val Met Ala Cys Val Lys His Phe Ile Gly Asn Glu
                180                 185                 190

Gln Glu Lys Tyr Arg Gln Pro Asp Asp Met Asn Pro Ala Thr Asn Gln
                195                 200                 205

Thr Thr Lys Glu Ala Ile Ser Ala Asn Ile Pro Asp Arg Ala Met His
210                 215                 220

Glu Leu Tyr Leu Trp Pro Phe Ala Asp Ser Val Arg Ala Gly Val Gly
225                 230                 235                 240

Ser Val Met Cys Ser Tyr Asn Arg Val Asn Asn Thr Tyr Ala Cys Glu
                245                 250                 255

Asn Ser Tyr Met Met Asn His Leu Leu Lys Glu Glu Leu Gly Phe Gln
                260                 265                 270

Gly Phe Val Val Ser Asp Trp Gly Ala Gln Leu Ser Gly Val Tyr Ser
                275                 280                 285

Ala Ile Ser Gly Leu Asp Met Ser Met Pro Gly Glu Val Tyr Gly Gly
                290                 295                 300

Trp Asn Thr Gly Thr Ser Phe Trp Gly Gln Asn Leu Thr Lys Ala Ile
305                 310                 315                 320

Tyr Asn Glu Thr Val Pro Ile Glu Arg Leu Asp Asp Met Ala Thr Arg
                325                 330                 335

Ile Leu Ala Ala Leu Tyr Ala Thr Asn Ser Phe Pro Thr Glu Asp His
                340                 345                 350

Leu Pro Asn Phe Ser Ser Trp Thr Thr Lys Glu Tyr Gly Asn Lys Tyr
                355                 360                 365

Tyr Ala Asp Asn Thr Thr Glu Ile Val Lys Val Asn Tyr Asn Val Asp
                370                 375                 380

Pro Ser Asn Asp Phe Thr Glu Asp Thr Ala Leu Lys Val Ala Glu Glu
385                 390                 395                 400

Ser Ile Val Leu Leu Lys Asn Glu Asn Asn Thr Leu Pro Ile Ser Pro
                405                 410                 415

Glu Lys Ala Lys Arg Leu Leu Leu Ser Gly Ile Ala Ala Gly Pro Asp
                420                 425                 430

Pro Ile Gly Tyr Gln Cys Glu Asp Gln Ser Cys Thr Asn Gly Ala Leu
```

```
              435                 440                 445
    Phe Gln Gly Trp Gly Ser Gly Ser Val Gly Ser Pro Lys Tyr Gln Val
        450                 455                 460
    Thr Pro Phe Glu Glu Ile Ser Tyr Leu Ala Arg Lys Ser Lys Met Gln
    465                 470                 475                 480
    Phe Asp Tyr Ile Arg Glu Ser Tyr Asp Leu Ala Gln Val Thr Lys Val
                    485                 490                 495
    Ala Ser Asp Ala His Leu Ser Ile Val Val Ser Ala Ser Gly
                500                 505                 510
    Glu Gly Tyr Ile Thr Val Asp Gly Asn Gln Gly Asp Arg Lys Asn Leu
                515                 520                 525
    Thr Leu Trp Asn Asn Gly Asp Lys Leu Ile Glu Thr Val Ala Glu Asn
        530                 535                 540
    Cys Ala Asn Thr Val Val Val Thr Ser Thr Gly Gln Ile Asn Phe
    545                 550                 555                 560
    Glu Gly Phe Ala Asp His Pro Asn Val Thr Ala Ile Val Trp Ala Gly
                    565                 570                 575
    Pro Leu Gly Asp Arg Ser Gly Thr Ala Ile Ala Asn Ile Leu Phe Gly
                580                 585                 590
    Lys Ala Asn Pro Ser Gly His Leu Pro Phe Thr Ile Ala Lys Thr Asp
                595                 600                 605
    Asp Asp Tyr Ile Pro Ile Glu Ile Tyr Ser Pro Ser Ser Gly Glu Pro
    610                 615                 620
    Glu Asp Asn His Leu Val Glu Asn Asp Leu Leu Val Asp Tyr Arg Tyr
    625                 630                 635                 640
    Phe Glu Glu Lys Asn Ile Glu Pro Arg Tyr Ala Phe Gly Tyr Gly Leu
                    645                 650                 655
    Ser Tyr Asn Glu Tyr Lys Val Ser Asn Ala Lys Val Ser Ala Ala Lys
                660                 665                 670
    Lys Val Asp Glu Glu Leu Pro Glu Pro Ala Thr Tyr Leu Ser Glu Phe
                675                 680                 685
    Ser Tyr Gln Asn Ala Lys Gly Ser Lys Asn Pro Ser Asp Ala Phe Ala
        690                 695                 700
    Pro Ala Asp Leu Asn Arg Val Asn Glu Tyr Leu Tyr Pro Tyr Leu Asp
    705                 710                 715                 720
    Ser Asn Val Thr Leu Lys Asp Gly Asn Tyr Glu Tyr Pro Asp Gly Tyr
                    725                 730                 735
    Ser Thr Glu Gln Arg Thr Thr Pro Ile Gln Pro Gly Gly Leu Gly
                740                 745                 750
    Gly Asn Asp Ala Leu Trp Glu Val Ala Tyr Lys Val Glu Val Asp Val
                755                 760                 765
    Gln Asn Leu Gly Asn Ser Thr Asp Lys Phe Val Pro Gln Leu Tyr Leu
        770                 775                 780
    Lys His Pro Glu Asp Gly Lys Phe Glu Thr Pro Val Gln Leu Arg Gly
    785                 790                 795                 800
    Phe Glu Lys Val Glu Leu Ser Pro Gly Glu Lys Thr Val Glu Phe
                    805                 810                 815
    Glu Leu Leu Arg Arg Asp Leu Ser Val Trp Asp Thr Ile Arg Gln Ser
                820                 825                 830
    Trp Ile Val Glu Ser Gly Thr Tyr Glu Ala Leu Ile Gly Val Ala Val
                835                 840                 845
    Asn Asn Ile Lys Thr Ser Val Leu Phe Thr Ile
        850                 855
```

<210> SEQ ID NO 12
<211> LENGTH: 859
<212> TYPE: PRT
<213> ORGANISM: Artificial Sequence
<220> FEATURE:
<223> OTHER INFORMATION: Description of Artificial Sequence: Synthetic SfBGL1-12 polypeptide

<400> SEQUENCE: 12

```
Val Pro Ile Gln Asn Tyr Thr Gln Ser Pro Ser Gln Gly Asp Glu Ser
1               5                   10                  15

Ser Gln Trp Val Ser Pro His Tyr Tyr Pro Thr Pro Gln Gly Gly Arg
            20                  25                  30

Leu Gln Asp Val Trp Gln Glu Ala Tyr Ala Arg Ala Lys Ala Ile Val
        35                  40                  45

Gly Gln Met Thr Ile Val Glu Lys Val Asn Leu Thr Thr Gly Thr Gly
    50                  55                  60

Trp Gln Leu Asp Pro Cys Val Gly Asn Ala Gly Ser Val Pro Arg Phe
65                  70                  75                  80

Gly Ile Pro Asn Leu Cys Leu Gln Asp Gly Pro Leu Gly Val Arg Phe
                85                  90                  95

Ala Asp Phe Val Thr Gly Tyr Pro Ser Gly Leu Ala Thr Gly Ala Thr
            100                 105                 110

Phe Asn Lys Asp Leu Phe Leu Gln Arg Gly Gln Ala Leu Gly His Glu
        115                 120                 125

Phe Asn Ser Lys Gly Val His Ile Ala Leu Gly Pro Ala Val Gly Pro
    130                 135                 140

Leu Gly Val Lys Ala Arg Gly Gly Arg Asn Phe Glu Ala Phe Gly Ser
145                 150                 155                 160

Asp Pro Tyr Leu Gln Gly Ile Ala Ala Ala Thr Ile Lys Gly Leu
                165                 170                 175

Gln Glu Asn Asn Val Met Ala Cys Val Lys His Phe Ile Gly Asn Glu
            180                 185                 190

Gln Glu Lys Tyr Arg Gln Pro Asp Asp Met Asn Pro Ala Thr Asn Gln
        195                 200                 205

Thr Thr Lys Glu Ala Ile Ser Ala Asn Ile Pro Asp Arg Ala Met His
    210                 215                 220

Glu Leu Tyr Leu Trp Pro Phe Ala Asp Ser Val Arg Ala Gly Val Gly
225                 230                 235                 240

Ser Val Met Cys Ser Tyr Asn Arg Val Asn Asn Thr Tyr Ala Cys Glu
                245                 250                 255

Asn Ser Tyr Met Met Asn His Leu Leu Lys Glu Glu Leu Gly Phe Gln
            260                 265                 270

Gly Phe Val Val Ser Asp Trp Ala Gln Leu Ser Gly Val Tyr Ser
        275                 280                 285

Ala Ile Ser Gly Leu Asp Met Ser Met Pro Gly Glu Val Tyr Gly Gly
    290                 295                 300

Trp Asn Thr Gly Thr Ser Phe Trp Gly Gln Asn Leu Thr Lys Ala Ile
305                 310                 315                 320

Tyr Asn Glu Thr Val Pro Ile Glu Arg Leu Asp Asp Met Ala Thr Arg
                325                 330                 335

Ile Leu Ala Ala Leu Tyr Ala Thr Asn Ser Phe Pro Thr Glu Asp His
            340                 345                 350

Leu Pro Asn Phe Ser Ser Trp Thr Thr Lys Glu Tyr Gly Asn Lys Tyr
```

```
                355                 360                 365
Tyr Ala Asp Asn Thr Thr Glu Ile Val Lys Val Asn Tyr Asn Val Asp
    370                 375                 380

Pro Ser Asn Asp Phe Thr Glu Asp Thr Ala Leu Lys Val Ala Glu Glu
385                 390                 395                 400

Ser Ile Val Leu Leu Lys Asn Glu Asn Asn Thr Leu Pro Ile Ser Pro
                405                 410                 415

Glu Lys Ala Lys Arg Leu Leu Leu Ser Gly Ile Ala Ala Gly Pro Asp
            420                 425                 430

Pro Ile Gly Tyr Gln Cys Glu Asp Gln Ser Cys Thr Asn Gly Ala Leu
        435                 440                 445

Phe Gln Gly Trp Gly Ser Gly Ser Val Gly Ser Pro Lys Tyr Gln Val
    450                 455                 460

Thr Pro Phe Glu Glu Ile Ser Tyr Leu Ala Arg Lys Ser Lys Met Gln
465                 470                 475                 480

Phe Asp Tyr Ile Arg Glu Ser Tyr Asp Leu Ala Gln Val Thr Lys Val
                485                 490                 495

Ala Ser Asp Ala His Leu Ser Ile Val Val Ser Ala Ala Ser Gly
            500                 505                 510

Glu Gly Tyr Ile Thr Val Asp Gly Asn Gln Gly Asp Arg Lys Asn Leu
        515                 520                 525

Thr Leu Trp Asn Asn Gly Asp Lys Leu Ile Glu Thr Val Ala Glu Asn
    530                 535                 540

Cys Ala Asn Thr Val Val Val Thr Ser Thr Gly Gln Ile Asn Phe
545                 550                 555                 560

Glu Gly Phe Ala Asp His Pro Asn Val Thr Ala Ile Val Trp Ala Gly
                565                 570                 575

Pro Leu Gly Asp Arg Ser Gly Thr Ala Ile Ala Asn Ile Leu Phe Gly
            580                 585                 590

Lys Ala Asn Pro Ser Gly His Leu Pro Phe Thr Ile Ala Lys Thr Asp
        595                 600                 605

Asp Asp Tyr Ile Pro Ile Glu Ile Tyr Ser Pro Ser Ser Gly Glu Pro
    610                 615                 620

Glu Asp Asn His Leu Val Glu Asn Asp Leu Leu Val Asp Tyr Arg Tyr
625                 630                 635                 640

Phe Glu Glu Lys Asn Ile Glu Pro Arg Tyr Ala Phe Gly Tyr Gly Leu
                645                 650                 655

Ser Tyr Asn Glu Tyr Lys Val Ser Asn Ala Lys Val Ser Ala Ala Lys
            660                 665                 670

Lys Val Asp Glu Glu Leu Pro Glu Pro Ala Thr Tyr Leu Ser Glu Phe
        675                 680                 685

Ser Tyr Gln Asn Ala Lys Gly Ser Lys Asn Pro Ser Asp Ala Phe Ala
    690                 695                 700

Pro Ala Asp Leu Asn Arg Val Asn Glu Tyr Leu Tyr Pro Tyr Leu Asp
705                 710                 715                 720

Ser Asn Val Thr Leu Lys Asp Gly Asn Tyr Glu Tyr Pro Asp Gly Tyr
                725                 730                 735

Ser Thr Glu Gln Arg Thr Thr Pro Ile Gln Pro Gly Gly Leu Gly
            740                 745                 750

Gly Asn Asp Ala Leu Trp Glu Val Ala Tyr Lys Val Glu Val Asp Val
        755                 760                 765

Gln Asn Leu Gly Asn Ser Thr Asp Lys Phe Val Pro Gln Leu Tyr Leu
    770                 775                 780
```

```
Lys His Pro Glu Asp Gly Lys Phe Glu Thr Pro Val Gln Leu Arg Gly
785                 790                 795                 800

Phe Glu Lys Val Glu Leu Ser Pro Gly Glu Lys Lys Thr Val Glu Phe
                805                 810                 815

Glu Leu Leu Arg Arg Asp Leu Ser Val Trp Asp Thr Ile Arg Gln Ser
            820                 825                 830

Trp Ile Val Glu Ser Gly Thr Tyr Glu Ala Leu Ile Gly Val Ala Val
        835                 840                 845

Asn Asn Ile Lys Thr Ser Val Leu Phe Thr Ile
850                 855

<210> SEQ ID NO 13
<211> LENGTH: 859
<212> TYPE: PRT
<213> ORGANISM: Artificial Sequence
<220> FEATURE:
<223> OTHER INFORMATION: Description of Artificial Sequence: Synthetic
      SfBGL1-14 polypeptide

<400> SEQUENCE: 13

Val Pro Ile Gln Asn Tyr Thr Gln Ser Pro Ser Gln Gly Asp Glu Ser
1               5                   10                  15

Ser Gln Trp Val Ser Pro His Tyr Tyr Pro Thr Pro Gln Gly Gly Arg
                20                  25                  30

Leu Gln Asp Val Trp Gln Glu Ala Tyr Ala Arg Ala Lys Ala Ile Val
            35                  40                  45

Gly Gln Met Thr Ile Val Glu Lys Val Asn Leu Thr Thr Gly Thr Gly
        50                  55                  60

Trp Gln Leu Asp Pro Cys Val Gly Asn Thr Gly Ser Val Pro Arg Phe
65                  70                  75                  80

Gly Ile Pro Asn Leu Cys Leu Gln Asp Gly Pro Leu Gly Val Arg Phe
                85                  90                  95

Ala Asp Phe Val Thr Gly Tyr Pro Ser Gly Leu Ala Thr Gly Ala Thr
            100                 105                 110

Phe Asn Lys Asp Leu Phe Leu Gln Arg Gly Gln Ala Leu Gly His Glu
        115                 120                 125

Phe Asn Ser Lys Gly Val His Ile Ala Leu Gly Pro Ala Val Gly Pro
    130                 135                 140

Leu Gly Val Lys Ala Arg Gly Gly Arg Asn Phe Glu Ala Phe Gly Ser
145                 150                 155                 160

Asp Pro Tyr Leu Gln Gly Ile Ala Ala Ala Thr Ile Lys Gly Leu
                165                 170                 175

Gln Glu Asn Asn Val Met Ala Cys Val Lys His Phe Ile Gly Asn Glu
            180                 185                 190

Gln Glu Lys Tyr Arg Gln Pro Asp Asp Met Asn Pro Ala Thr Asn Gln
        195                 200                 205

Thr Thr Lys Glu Ala Ile Ser Ala Asn Ile Pro Asp Arg Ala Met His
    210                 215                 220

Glu Leu Tyr Leu Trp Pro Phe Ala Asp Ser Val Arg Ala Gly Val Gly
225                 230                 235                 240

Ser Val Met Cys Ser Tyr Asn Arg Val Asn Asn Thr Tyr Ala Cys Glu
                245                 250                 255

Asn Ser Tyr Met Met Asn His Leu Leu Lys Glu Glu Leu Gly Phe Gln
            260                 265                 270

Gly Phe Ala Val Ser Asp Trp Gly Ala Gln Leu Ser Gly Val Tyr Ser
```

```
                    275                 280                 285
Ala Ile Ser Gly Leu Asp Met Ser Met Pro Gly Glu Val Tyr Gly Gly
            290                 295                 300
Trp Asn Thr Gly Thr Ser Phe Trp Gly Gln Asn Leu Thr Lys Ala Ile
305                 310                 315                 320
Tyr Asn Glu Thr Val Pro Ile Glu Arg Leu Asp Asp Met Ala Thr Arg
                325                 330                 335
Ile Leu Ala Ala Leu Tyr Ala Thr Asn Ser Phe Pro Thr Glu Asp His
            340                 345                 350
Leu Pro Asn Phe Ser Ser Trp Thr Thr Lys Glu Tyr Gly Asn Lys Tyr
            355                 360                 365
Tyr Ala Asp Asn Thr Thr Glu Ile Val Lys Val Asn Tyr Asn Val Asp
        370                 375                 380
Pro Ser Asn Asp Phe Thr Glu Asp Thr Ala Leu Lys Val Ala Glu Glu
385                 390                 395                 400
Ser Ile Val Leu Leu Lys Asn Glu Asn Asn Thr Leu Pro Ile Ser Pro
                405                 410                 415
Glu Lys Ala Lys Arg Leu Leu Leu Ser Gly Ile Ala Ala Gly Pro Asp
            420                 425                 430
Pro Ile Gly Tyr Gln Cys Glu Asp Gln Ser Cys Thr Asn Gly Ala Leu
            435                 440                 445
Phe Gln Gly Trp Gly Ser Gly Ser Val Gly Ser Pro Lys Tyr Gln Val
        450                 455                 460
Thr Pro Phe Glu Glu Ile Ser Tyr Leu Ala Arg Lys Ser Lys Met Gln
465                 470                 475                 480
Phe Asp Tyr Ile Arg Glu Ser Tyr Asp Leu Ala Gln Val Thr Lys Val
                485                 490                 495
Ala Ser Asp Ala His Leu Ser Ile Val Val Ser Ala Ala Ser Gly
            500                 505                 510
Glu Gly Tyr Ile Thr Val Asp Gly Asn Gln Gly Asp Arg Lys Asn Leu
            515                 520                 525
Thr Leu Trp Asn Asn Gly Asp Lys Leu Ile Glu Thr Val Ala Glu Asn
        530                 535                 540
Cys Ala Asn Thr Val Val Val Thr Ser Thr Gly Gln Ile Asn Phe
545                 550                 555                 560
Glu Gly Phe Ala Asp His Pro Asn Val Thr Ala Ile Val Trp Ala Gly
                565                 570                 575
Pro Leu Gly Asp Arg Ser Gly Thr Ala Ile Ala Asn Ile Leu Phe Gly
            580                 585                 590
Lys Ala Asn Pro Ser Gly His Leu Pro Phe Thr Ile Ala Lys Thr Asp
            595                 600                 605
Asp Asp Tyr Ile Pro Ile Glu Ile Tyr Ser Pro Ser Ser Gly Glu Pro
        610                 615                 620
Glu Asp Asn His Leu Val Glu Asn Asp Leu Leu Val Asp Tyr Arg Tyr
625                 630                 635                 640
Phe Glu Glu Lys Asn Ile Glu Pro Arg Tyr Ala Phe Gly Tyr Gly Leu
                645                 650                 655
Ser Tyr Asn Glu Tyr Lys Val Ser Asn Ala Lys Val Ser Ala Ala Lys
            660                 665                 670
Lys Val Asp Glu Glu Leu Pro Glu Pro Ala Thr Tyr Leu Ser Glu Phe
            675                 680                 685
Ser Tyr Gln Asn Ala Lys Gly Ser Lys Asn Pro Ser Asp Ala Phe Ala
        690                 695                 700
```

-continued

```
Pro Ala Asp Leu Asn Arg Val Asn Glu Tyr Leu Tyr Pro Tyr Leu Asp
705                 710                 715                 720

Ser Asn Val Thr Leu Lys Asp Gly Asn Tyr Glu Tyr Pro Asp Gly Tyr
            725                 730                 735

Ser Thr Glu Gln Arg Thr Thr Pro Ile Gln Pro Gly Gly Gly Leu Gly
            740                 745                 750

Gly Asn Asp Ala Leu Trp Glu Val Ala Tyr Lys Val Glu Val Asp Val
        755                 760                 765

Gln Asn Leu Gly Asn Ser Thr Asp Lys Phe Val Pro Gln Leu Tyr Leu
    770                 775                 780

Lys His Pro Glu Asp Gly Lys Phe Glu Thr Pro Val Gln Leu Arg Gly
785                 790                 795                 800

Phe Glu Lys Val Glu Leu Ser Pro Gly Glu Lys Lys Thr Val Glu Phe
                805                 810                 815

Glu Leu Leu Arg Arg Asp Leu Ser Val Trp Asp Thr Ile Arg Gln Ser
                820                 825                 830

Trp Ile Val Glu Ser Gly Thr Tyr Glu Ala Leu Ile Gly Val Ala Val
            835                 840                 845

Asn Asn Ile Lys Thr Ser Val Leu Phe Thr Ile
            850                 855
```

MUTANT BETA-GLUCOSIDASES HAVING ENHANCED ACTIVITY AND A METHOD FOR PRODUCING BIOETHANOL USING THE SAME

RELATED APPLICATIONS

This application is a 35 U.S.C. §371 filing of International Application No. PCT/KR2012/002846, filed Apr. 12, 2013; which claims priority to Korean Patent Application No. 10-2011-0034162, filed on Apr. 13, 2011. The entire contents of each are incorporated herein by reference.

SEQUENCE LISTING

This application contains a Sequence Listing in computer readable format. The Sequence Listing is provided as a file entitled 551716_HNT-027_sequence_listing_ST25.txt, created Jan. 24, 2017, which is 38,909 bytes in size. The information in the computer readable format of the Sequence Listing is incorporated herein by reference in its entirety.

BACKGROUND OF THE INVENTION

1. Field of the Invention

The present invention relates to beta-glucosidase that is mutated to have enhanced activity, and a method for producing bioethanol using the same. More particularly, the present invention relates to a polynucleotide encoding beta-glucosidase that is mutated to have enhanced activity, beta-glucosidase expressed from the polynucleotide, an expression vector including the polynucleotide, a transformant that is transformed with the expression vector, a method for producing the mutated beta-glucosidase using the transformant, and a method for producing bioethanol using the transformant.

2. Description of the Related Art

Worldwide, efforts are ongoing to obtain the bio-energy from inexpensive, renewable biomass because of the problems of the depletion of crude oil and global warming. Cellulosic biomass is the most abundant organic material on Earth, and is a renewable raw material capable of producing a variety of energy and raw material platform compounds, which have been conventionally produced from the petroleum-based materials (Hoffer, et al., 2002, Science, 298, 981). The process of obtaining bio-energy, particularly, bio-ethanol from cellulosic biomass is technically possible, but it is expensive and lacks important benefits considering the current crude oil price (Zaldivar et al., 2001, Appl. Microbiol. Biotechnol., 56, 17). Bioethanol is obtained from cellulosic biomass by decomposition of biomass and fermentation of the decomposed sugar, but naturally occurring microorganisms cannot decompose and ferment biomass in a high yield at the same time. Inefficiently, the current technology consists of two steps, decomposition (saccharification) and fermentation of biomass (Lynd et al., 2002, Microbiol. Mol. Biol. Rev. 66, 506).

Because cellulosic biomass has a very solid structure and its natural decomposition occurs very slowly, it is required to perform pretreatment and expensive cellulase treatment processes in order to artificially speed up the decomposition (Lynd et al., 1999, Biotechnol. Prog. 15, 777, Himmel et al., 2007, Science, 315, 804). Therefore, in order to ensure economic feasibility in the production of bioenergy and platform compounds using cellulose biomass, it is required to develop a low-cost mass production technology of cellulases for efficient decomposition of cellulose biomass, in particular, a consolidated bioprocess (CBP) technology of directly utilizing the enzyme-producing recombinant strain in the bioenergy production technology (Hahn-Hagerdal et al., 2006, Trends Biotechnol, 24, 549, Lynd et al., 2008, Nat. Biotechnol., 26, 169).

Cellulosic biomass has a very solid and stable structure, because it is mainly composed of cellulose as a glucose polymer, hemicellulose as a xylose polymer, and lignin. For efficient enzymatic decomposition of cellulosic biomass, it is necessary to perform a physicochemical pretreatment of the biomass to disintegrate the stable structure of the plant, thereby allowing better access to substrate by the enzyme. A number of different types of cellulases are necessary, depending on the type of the substrate. For degradation of cellulose, endocellulase (endo-1,4-β-D-glucanase), exocellulase (exo-1,4-β-D-glucanase or cellobiohydrolase) and beta-glucosidase (β-glucosidase or cellobiase) are essential (Kubicek et al., 1992, Adv. Biochem. Eng. Biotechnol. 45, 1). For degradation of hemicellulose, endoxylanase (endo-1,4-β-xylanase) and beta-xylosidase (β-xylosidase) are needed as representative essential enzymes, and a variety of de-branching enzymes are required for complete degradation of cellulosic biomass. These enzymes are found in the microorganisms, in particular, fungi which naturally degrade plants. A commercially available cellulase is an enzyme complex derived from the fungus *Trichoderma reesei*, which has been commercialized by Novozymes and Danisco.

At present, the biomass-degrading enzyme for bioenergy production has been exclusively produced and sold by the two aforementioned multinational corporations in the world. However, the enzyme is considerably expensive, and it is not optimized for the type of biomass. Thus, there is a problem that an excessive amount of enzyme should be used for complete decomposition of cellulosic biomass (Merino and Cherry, 2007, Adv. Biochem. Eng. Biotechnol. 108, 95, Kabel et al., 2006, Bioeng. Biotechnol. 93, 56).

Therefore, when each enzyme is produced using a recombinant host system such as bacteria or yeast, it can be used in combinations optimized for the type of biomass, reducing the use of commercial enzymes. The yeast *Saccharomyces cerevisiae* as the host cell for the production of recombinant enzymes has superior ethanol-fermenting ability and frequently used as an ethanol-producing strain. Many studies have been made to introduce a cellulose-degrading ability into this strain and to produce recombinant cellulases (Lynd et al., 2002, Microbiol. Mol. Biol. Rev., 66, 506). However, since this strain has no cellulase productivity, its applicability in the mass-production of the recombinant cellulases is low.

As such, the yeast is very excellent in the conventional bioethanol fermentation, but it has no cellulose biomass-degrading ability. Thus, when non-food cellulosic biomass is used as a raw material for the production of bioenergy, the use of expensive cellulase is inevitably needed. In order to solve this problem, numerous studies have been conducted to develop a recombinant strain that is introduced with a foreign cellulase gene. However, its low enzyme productivity generates a problem that the cellulose substrate in the medium is not efficiently degraded by the enzymes produced. Consequently, there has been a limit in the production of bioethanol using the resulting sugar.

Accordingly, in order to solve these problems, the present inventors have prepared beta-glucosidase that is mutated to have enhanced activity, and produced a large amount of beta-glucosidase using a translational fusion partner technology which is a technology for high secretory production of the yeast recombinant protein, and they also used the recombinant enzyme-producing strain to develop an efficient CBP technology for bioethanol production based on high concentration of cellobiose and a cost-effective simultaneous saccharification and fermentation (SSF) technology for bioethanol production, thereby completing the present invention.

SUMMARY OF THE INVENTION

An object of the present invention is to provide a polynucleotide encoding beta-glucosidase that is mutated to have enhanced activity.

Another object of the present invention is to provide beta-glucosidase that is expressed from the polynucleotide encoding the mutated beta-glucosidase.

Still another object of the present invention is to provide an expression vector including the polynucleotide.

Still another object of the present invention is to provide a transformant that is transformed with the expression vector.

Still another object of the present invention is to provide a method for producing beta-glucosidase that is mutated to have enhanced activity, comprising the steps of culturing the transformant, and recovering beta-glucosidase from a culture or culture supernatant thereof.

Still another object of the present invention is to provide a method for producing bioethanol using the transformant that is transformed by introduction of the expression vector into a host cell having an ethanol-fermenting ability.

BRIEF DESCRIPTION OF THE DRAWINGS

FIG. 9b is an image showing the result of pNPG assay of mutant libraries;

DETAILED DESCRIPTION OF THE PREFERRED EMBODIMENTS

Figure 1:
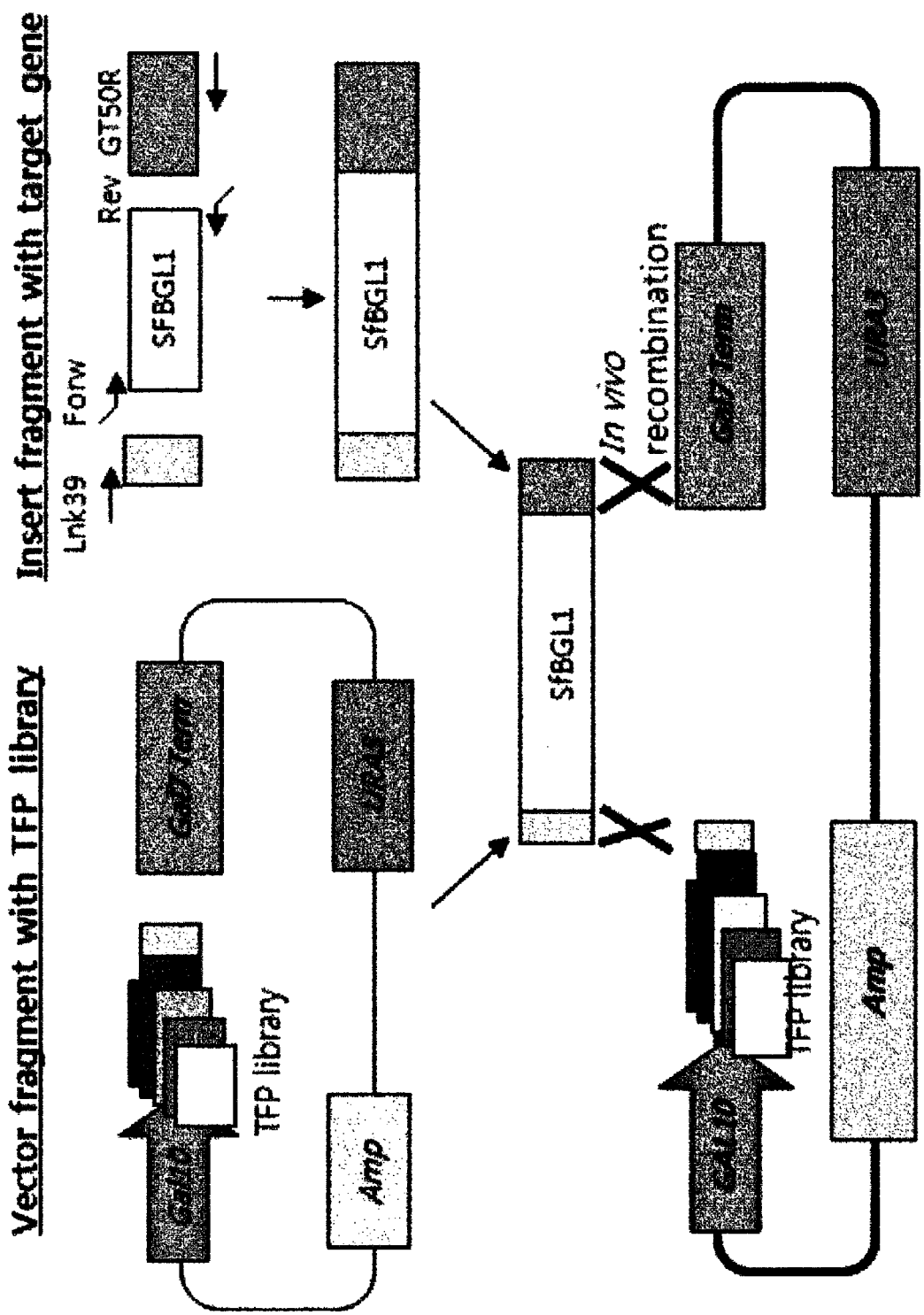
FIG. 1 is a schematic diagram of polymerase chain reaction (PCR) and in vivo recombination for introduction of the SfBGL1 gene into the yeast TFP vector.

In one aspect to achieve the above objects, the present invention provides beta-glucosidase that is mutated to have enhanced activity.

As used herein, the term "beta-glucosidase that is mutated to have enhanced activity" means beta-glucosidase having a mutated amino acid sequence in order to enhance the intrinsic activity of beta-glucosidase which degrades glycoside or oligosaccharide to produce monosaccharide.

The mutated amino acid sequence may be, but is not particularly limited to, preferably an amino acid sequence of beta-glucosidase that is expressed from a polynucleotide that is mutated by substitution of adenine with guanine at position 114, by substitution of thymine with cytosine at position 1377, by substitution of thymine with adenine at position 1527, by substitution of thymine with cytosine at position 2251, or by combinations thereof in the polynucleotide of SfBGL1 derived from Saccharomycopsis fiburigera or in the polynucleotide sequence of SEQ ID NO. 8, or the polynucleotide sequence of SEQ ID NO. 9. Also, the mutated amino acid sequence may be an amino acid sequence that is mutated by substitution of threonine (T) with alanine (A) at position 74, by substitution of valine (V) with alanine (A) at position 275, or by substitution of both amino acids with alanine (A) at positions 74 and 275 in the amino acid sequence of beta-glucosidase expressed from a gene composed of the polynucleotide sequence of SEQ ID NO. 8.

In another aspect of the present invention, the present invention provides a polynucleotide encoding the mutated beta-glucosidase.

As used herein, the term "polynucleotide", is a DNA (deoxyribonucleic acid) or RNA (ribonucleic acid) strand having more than a certain length as a nucleotide polymer which is a long chain of nucleotide monomers connected by a covalent bond, refers to a polynucleotide encoding the mutated beta-glucosidase.

The polynucleotide encoding the mutated beta-glucosidase may be, but is not particularly limited to, preferably a polynucleotide that is mutated by substitution of adenine with guanine at position 114, by substitution of thymine with cytosine at position 1377, by substitution of thymine with adenine at position 1527, by substitution of thymine with cytosine at position 2251, or by combinations thereof in the polynucleotide sequence of beta-glucosidase gene (SEQ ID NO. 8) derived from Saccharomycopsis fiburigera, or a nucleotide sequence encoding the polypeptide that is prepared by substitution of threonine (T) with alanine (A) at position 74, by substitution of valine (V) with alanine (A) at position 275, or by substitution of both amino acids with alanine (A) at positions 74 and 275 in the polypeptide expressed from the polynucleotide of SEQ ID NO. 8.

In still another aspect of the present invention, the present invention provides an expression vector including the polynucleotide encoding the mutated beta-glucosidase.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated.

The vector of the present invention is able to direct the expression of a gene encoding the desired protein which is operatively-linked. Such vector is referred to herein as "expression vectors". In general, expression vectors in the use of recombinant DNA techniques are often in the form of plasmids.

As used herein, the terms "plasmid" and "vector" can be used interchangeably as the plasmid and the plasmid is the most commonly used form of vector.

The type of the usable expression vector can be determined depending on the host cells. When yeast is used as a host, examples of the expression vector may include YEp13, YCp50, pRS-based vectors, pYEX-based vectors or the like.

Examples of the promoter may include a GAL promoter, an AGO promoter or the like.

Examples of the method for introducing the recombinant DNA into yeast may include an electroporation method (Method Enzymol., 194, 182-187 (1990)), a spheroplast method (Proc. Natl. Acad. Sci. USA, 84, 1929-1933 (1978)), a lithium acetate method (J. Bacteriol., 153, 163-168 (1983)) or the like.

Moreover, the expression vector may further include an expression-suppressing fragment having a variety of functions for suppression, amplification or induction of the desired gene expression, a selectable marker or an antibiotic resistance gene for selection of transformants, a gene encoding a secretion signal, a tailored fusion partner for non-producible protein or the like.

In particular, the tailored fusion partner for non-producible protein is preferably a translational fusion partner (TFP), and the tailored fusion partner usable in the present invention is disclosed in Korean Patent NOs. 0626753, 0798394, and 0975596.

As used herein, the term, "translational fusion partner (TFP)" refers to a gene that is fused to a gene encoding a non-producible protein and induces the secretory production of the non-producible protein. The translational fusion partner can be selected from DNAs of all prokaryotes or eukaryotes including bacteria (e.g., Escherichia sp., Pseudomonas sp., Bacillus sp., etc.), fungi (e.g., yeast, Aspergillus sp., Penicillium sp., Rhizopus sp., Trichoderma sp., etc.), plants (e.g., Arabidopsis thaliana, corn, tobacco, potato, etc.) and animals (e.g., human, mouse, rat, rabbit, dog, cat, monkey, etc.).

In specific embodiment of the present invention, in order to examine the fusion partners of the recombinant vector for efficient secretory production of the mutated beta-glucosidase having enhanced activity of the present invention, its own signal, MFα (mating factor alpha) or translational fusion partner (STF19) was used as a fusion partner to analyze the beta-glucosidase activity (Table 3). As a result, STF19 was identified as the optimum fusion partner (Table 3 and FIG. 7).

In still another aspect of the present invention, the present invention provides a transformant that is transformed by introduction of the expression vector into a host cell.

As used herein, the term "transformation" means introduction of DNA into a suitable host cell so that the DNA is replicable, either as an extrachromosomal element, or by chromosomal integration.

The host cell used in the transformation according to the present invention may be any host cell that is widely known in the art. A host that is excellent in the introduction of the mutated beta-glucosidase gene of the present invention and has high expression efficiency of the introduced gene can be used, and examples thereof may include bacteria, fungi (e.g., yeast), plants or animals (e.g., mammals or insects).

Preferably, the host cell may be a cell having an ethanol-fermenting ability. More preferably, the cell having an ethanol-fermenting ability may be *Zymomonas*, yeast, or *Bacillus*.

The yeast may include, but is not particularly limited to, microorganisms belonging to *Candida* sp., *Debaryomyces* sp., *Hansenula* sp., *Kluyveromyces* sp., *Pichia* sp., *Schizosaccharomyces* sp., *Yarrowia* sp., *Saccharomyces* sp., *Saccharomycopsis* sp., *Schwanniomyces* sp., or *Arxula* sp. More preferably, *Candida utilis*, *Candida boidinii*, *Candida albicans*, *Kluyveromyces lactis*, *Pichia pastoris*, *Pichia stipitis*, *Schizosaccharomyces pombe*, *Saccharomyces cerevisiae*, *Saccharomycopsis fiburigera*, *Hansenula polymorpha*, *Yarrowia lipolytica*, *Schwanniomyces occidentalis*, *Arxula adeninivorans* or the like may be used. Most preferably, *Kluyveromyces marxianus* 7155, *Saccharomyces cerevisiae*, or *Saccharomycopsis fiburigera* may be used.

Figure 9A:
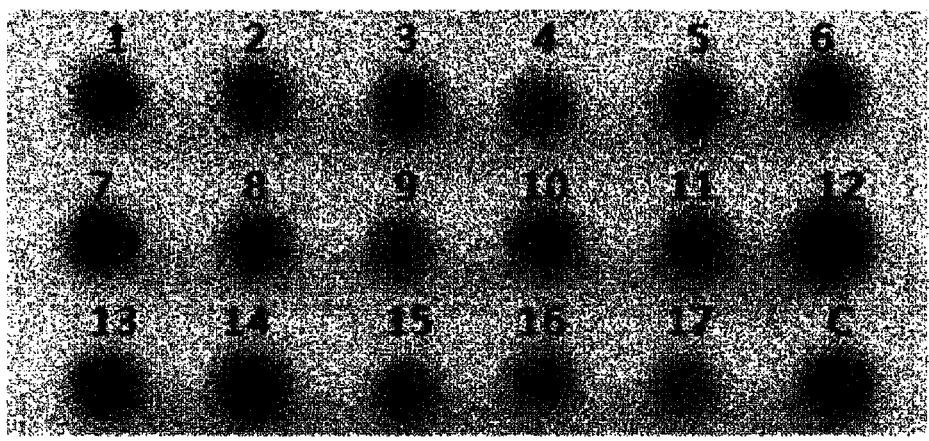
FIG. 9a is an image showing the result of EGDA assay of mutant libraries.

In the specific embodiment of the present invention, the enzymatic activity of the expressed beta-glucosidase was measured by EGDA and pNPG assays. As a result, the yeast transformant that was introduced with the polynucleotide encoding the beta-glucosidase being mutated to have the enhanced activity according to the present invention was found to produce beta-glucosidase having a higher enzymatic activity than non-transformed yeast strain (Table 4, FIGS. 9a and 9b).

In still another aspect of the present invention, the present invention provides a method for producing beta-glucosidase that is mutated to have enhanced activity, including the steps of culturing the transformant, and recovering the mutated beta-glucosidase from a culture or culture supernatant thereof.

In this regard, the step of recovering the mutated beta-glucosidase may be performed by the known purification method such as homogenization, extraction, affinity chromatography, ion exchange chromatography, gel filtration chromatography, hydrophobic chromatography, protein precipitation, or dialysis of the cultured cells or the culture supernatant obtained from the culture, either singly or in any combination thereof. The desired protein thus recovered may be identified by the typically known method such as SDS-PAGE, Western blotting or the like.

In still another aspect of the present invention, the present invention provides a method for producing bioethanol, including the steps of culturing the transformant in the presence of a beta-glucosidase substrate, and recovering bioethanol therefrom.

Specifically, the method for producing bioethanol of the present invention includes the steps of (i) introducing the expression vector into a host cell having an ethanol-fermenting ability to obtain a transformant; (ii) culturing the transformant thus obtained in a culture medium containing a beta-glucosidase substrate; and (iii) recovering bioethanol from the culture or culture supernatant obtained in step (ii).

In this regard, the host cell having the ethanol-fermenting ability is, but not particularly limited to, preferably a *Zymomonas* (*Zymomonas Mobilis*) strain, a yeast strain, and a *Bacillus* strain that are known to have the ethanol-fermenting ability.

The substrate is, but not particularly limited to, preferably glucoside, oligosaccharide, biomass or the like that can be degraded by beta-glucosidase. More preferably, the substrate is maltose, trehalose, sucrose, turanose, lactose, cellobiose, maltotriose, raffinose, kestose, cellulose-based agricultural biomass (palm fruit by-products such as EFB, Jerusalem artichokes tuber, etc.), seaweed-derived biomass (Gelidium cellulose, etc.), or the like. They may be used either singly or in any combination thereof.

The culture method is, but not particularly limited to, any method typically used in the culture of microorganisms, such as a batch-type, a fed-batch type, a continuous culture, a reactor-type culture or the like.

Further, in the specific embodiment of the present invention, the yeast transformant that is transformed with the expression vector introduced with the polynucleotide according to the present invention was used to perform fermentation using glucose and cellobiose as substrates. As a result, it was found that ethanol could be more effectively produced by using cellobiose or glucose as a substrate (FIGS. 12a and 12b), when beta-glucosidase was expressed. And ethanol could be also effectively produced by using a cellulose-based agricultural biomass and a seaweed-derived biomass as a substrate, such as palm fruit by-products (EFB), Jerusalem artichokes tuber, Gelidium cellulose, etc. (FIGS. 15a to 17b).

Hereinafter, the present invention will be described in more detail with reference to Examples. However, these Examples are for illustrative purposes only, and the invention is not intended to be limited by these Examples.

Example 1. Cloning of Beta-Glucosidase (β-Glucosidase) Gene

In order to clone *Saccharomycopsis fiburigera*-derived beta-glucosidase (SfBGL) gene, the *Saccharomycopsis fiburigera* KCTC 7938 strain was provided by Genbank at Korea Research Institute of Bioscience and Biotechnology, Daejeon and cultured in an YPD (1% yeast extract, 2% peptone, 2% glucose) medium, followed by extraction of genomic DNA. 1 μl of the extracted sample as a template and a sense primer H574 (SEQ ID NO. 1) and an antisense primer H576 (SEQ ID NO. 2) were used to perform polymerase chain reaction (PCR) (1 cycle of 94° C. for 5 minutes; 25 cycles of 94° C. for 30 seconds, 55° C. for 30 seconds, 72° C. for 3 minutes, 72° C. for 1 minute; 1 cycle of 72° C. for 7 minutes).

```
H574:
                                    (SEQ ID NO. 1)
5'-catgaattcaaaatgttgatgatagtacag-3'

H576:
                                    (SEQ ID NO. 2)
5'-ctgccgagacctttgcattgc-3'
```

Next, agarose gel electrophoresis of the gene thus amplified was performed to obtain a 2.6-kb fragment. The PCR product was cloned into a pGEM-T Easy vector (promega) to prepare a plasmid pT-SfBGL1, followed by sequence analysis.

As a result, *Saccharomycopsis fiburigera*-derived beta-glucosidase (β-glucosidase) gene, SfBGL1 was identified (SEQ ID NO. 8), which is different from the known sequence (ACH90244) registered in Genbank having 11 different amino acids.

Example 2. Secretory Production of Beta-Glucosidase by Use of Translational Fusion Partner (TFB)

In order to express the beta-glucosidase (β-glucosidase) gene SfBGL1 thus identified in Example 1 in yeast *Saccharomyces cerevisiae* (*S. cerevisiae*), primary PCR was performed using pT-SfBGL1 as a template and JJ12 (SEQ ID NO. 3) and JJ13 (SEQ ID NO. 4) as primers for obtaining a beta-glucosidase gene without its own secretion signal. In order to introduce a sequence complementary to the terminus of the yeast vector into the gene, secondary PCR was performed using LNK39 and GT50R as primers to prepare a gene for in vivo recombination with the vector (FIG. 1). FIG. 1 is a schematic diagram of PCR and in vivo recombination for introduction of the SfBGL1 gene into the yeast TFP vector.

```
JJ12:
                                        (SEQ ID NO. 3)
5'-ctcgccttagataaaagagtcccaattcaaaactatac-3'

JJ13:
                                        (SEQ ID NO. 4)
5'-cactccgttcaagtcgacttaaatagtaaacaggacag-3'

LNK39:
                                        (SEQ ID NO. 5)
5'-ggccgcctcggcctctgctggcctcgccttagataaaaga-3'

GT50R:
                                        (SEQ ID NO. 6)
5'-gtcattattaaatatatatatatatatattgtcactccgttcaag
tcgac-3'
```

Figure 2:
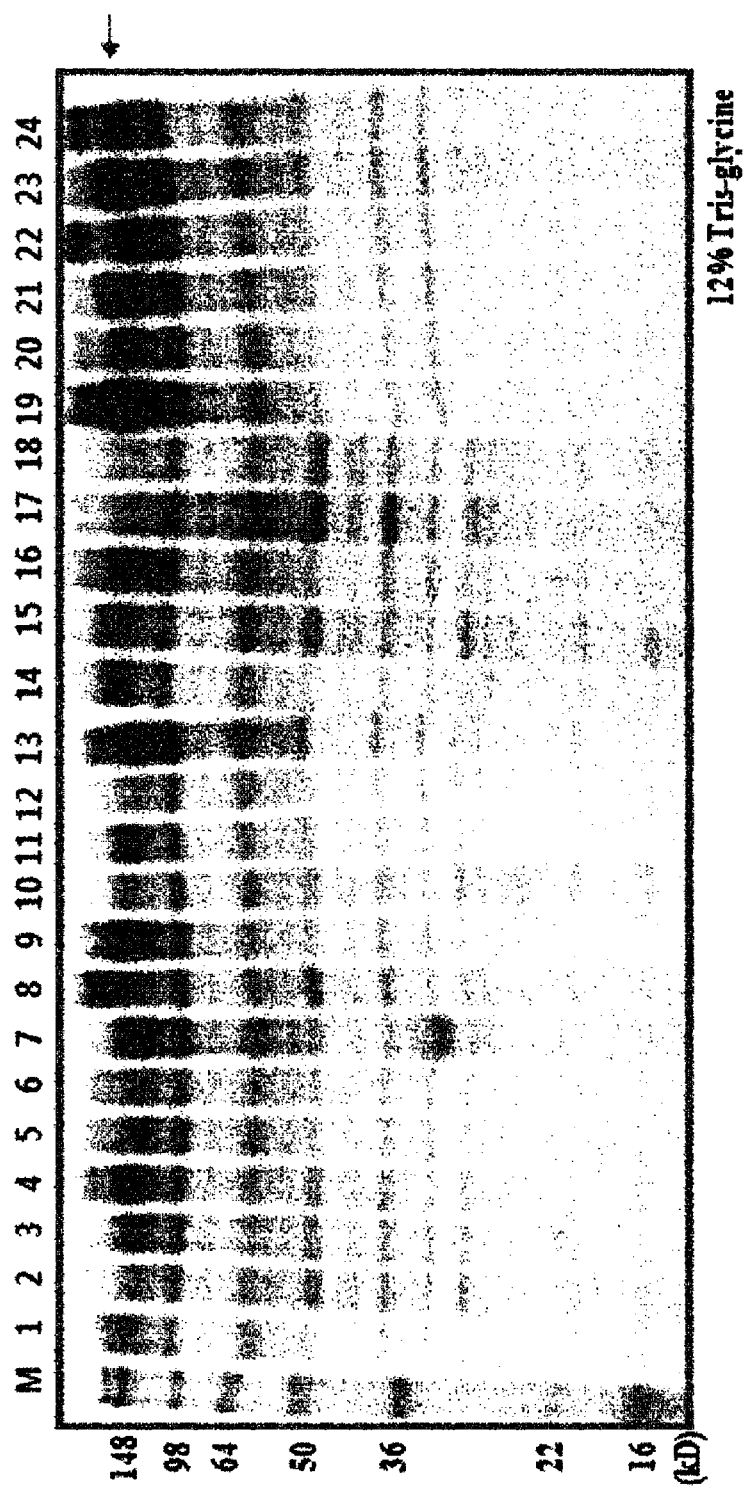
FIG. 2 is an electrophoresis image showing the results of SDS-PAGE of the supernatants of 24 transformants that were prepared by introduction of SfBGL1 into the yeast Y2805 strain.

The expression vector (YGaSfBGL1) including the amplified gene and the vector containing 24 types of TFPs for secretory expression of proteins were introduced into the yeast strain Y2805 (Mat a pep4::HIS3 prb1 can1 his3-200 ura3-52) to prepare transformants by in vivo recombination. PCR products amplified using the primers LNK39 (SEQ ID NO. 5) and GT50R (SEQ ID NO. 6) includes sequences of more than 40 bases identical to that of the vector. Thus, when they are introduced into the yeast cells, together with the linear vector, circular plasmid vectors are formed by in vivo recombination (FIG. 1). The transformants was selected on a uracil-free selective medium (0.67% amino acid-deficient yeast substrate, 0.77% uracil-deficient nutritional supplements, 2% glucose). The cells were cultured in an YPDG (1% yeast extract, 2% peptone, 1% glucose, 1% galactose) medium for 40 hours, and then 0.6 ml of supernatant was precipitated with 0.4 ml of acetone, followed by SDS-PAGE analysis (FIG. 2). FIG. 2 is an electrophoresis image showing the results of SDS-PAGE of the supernatants of 24 transformants that were prepared by introduction of SfBGL1 into the yeast Y2805 strain. The strong protein bands are considerably different in size from the protein inferred from the SfBGL1 gene, suggesting that the difference is attributed to additional sugar chains caused by 14 N-glycosylation sites on the SfBGL1 protein sequence.

In order to examine the activity of the secreted protein, 0.1 ml of an enzyme solution was reacted with 0.9 ml of a substrate solution (100 mM citrate-phosphate buffer solution (pH 5.0), 1 mM p-nitrophenyl-β-D-glucopyranoside (pNPG)) at 50° C. for 10 minutes. Subsequently, an equal quantity of 30% sodium carbonate solution was added to terminate the reaction, and absorbance was measured at 410 nm to select transformants having high beta-glucosidase activity (FIG. 1). In this regard, one unit of beta-glucosidase activity was defined as the amount of enzyme liberating 1 μM of p-nitrophenol per minute.

TABLE 1

Analysis of beta-glucosidase activity of strain having each expression vector

| No. | Beta-glucosidase activity (U/ml) |
|---|---|
| 1 | 229 |
| 2 | 0 |
| 3 | 156 |
| 4 | 664 |
| 5 | 155 |
| 6 | 262 |
| 7 | 542 |
| 8 | 638 |
| 9 | 947 |
| 10 | 18 |
| 11 | 328 |
| 12 | 0 |
| 13 | 464 |
| 14 | 296 |
| 15 | 84 |
| 16 | 327 |
| 17 | 0 |
| 18 | 0 |
| 19 | 1256 |
| 20 | 603 |
| 21 | 867 |
| 22 | 772 |
| 23 | 496 |
| 24 | 406 |

As shown in FIG. 1, it was found that the transformants (ST9-SfBGL1, ST19-SfBGL1, ST21-SfBGL1 and ST22-SfBGL1) introduced with SfBGL1 and the TFPNOs. 9, 19, 21 and 22 among the 24 TFPs expressed beta-glucosidase having relatively higher activity, and the transformant (ST19-SfBGL1) introduced with SfBGL1 and the TFPNO. 19 expressed beta-glucosidase having the most excellent activity.

Example 3: Secretory Production of Beta-Glucosidase by Use of Y2805ΔGal80 Strain

Example 3-1: Preparation of Mutated Y2805ΔGal80 Strain and Secretory Production of Beta-Glucosidase by Use of Mutated Y2805ΔGal80 Strain The GAL promoter contained in the expression vector requires galactose that is approximately 20-fold more expensive than glucose for the expression as an inducer. In order to solve this problem, the strain Y2805Δgal80, which does not require galactose for expression of GAL promoter, was used.

Figure 3:
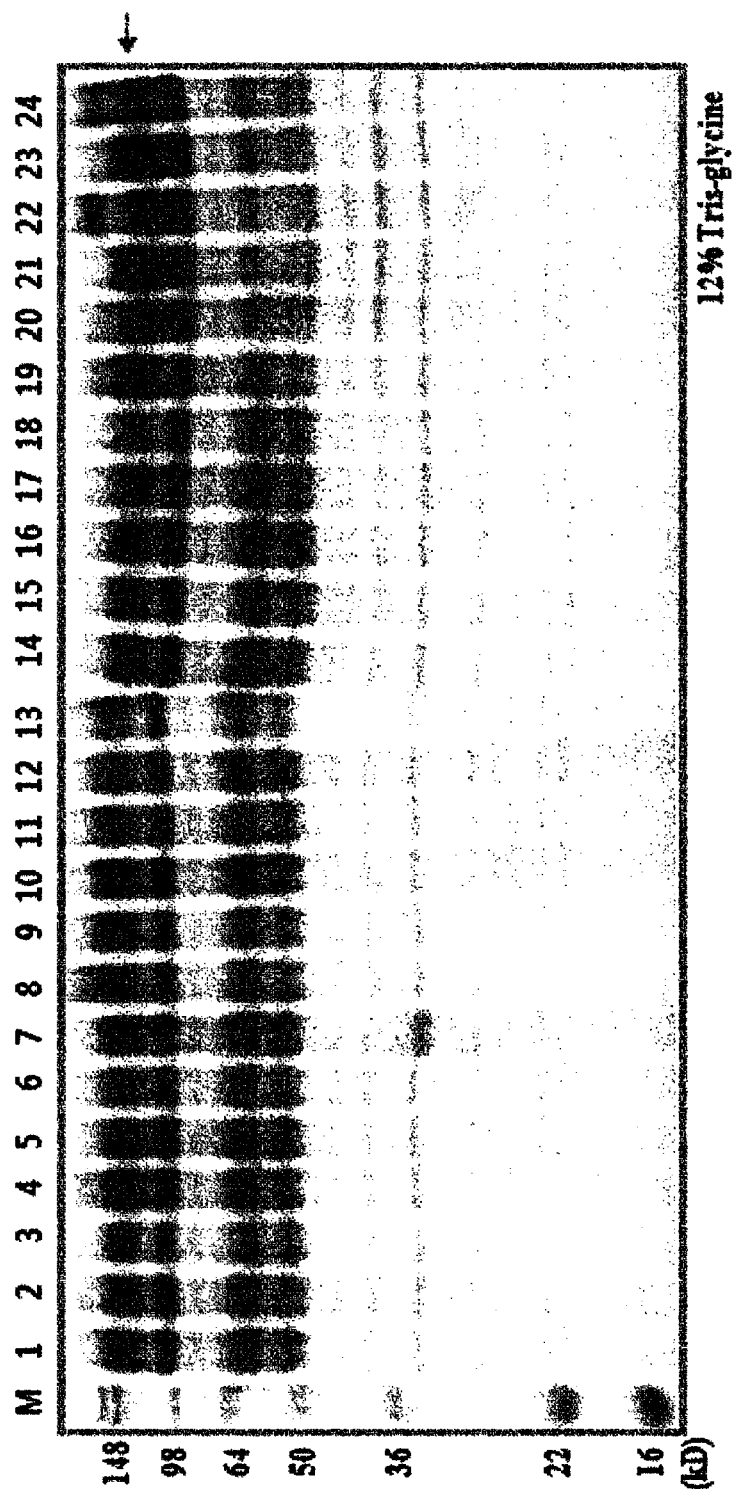
FIG. 3 is an electrophoresis image showing the results of SDS-PAGE of the supernatants of 24 transformants that were prepared by introduction of SfBGL1 into the yeast Y2805Δgal80 strain.

In detail, 24 types of transformants (Y2805Δgal80/ST1-SfBGL1 to Y2805Δgal80/ST24-SfBGL1) introduced with SfBGL1 and 24 types of TFPs were obtained in the same manner as in Example 2, except that Y2805Δgal80 (Mat a pep4::HIS3 gal80::Tc190, prb1 can1 his3-200 ura3-52) strain was used instead of Y2805 strain. The transformants thus obtained were cultured in the YPD (1% yeast extract, 2% peptone, 2% glucose) medium for 40 hours, and each of the culture broths was centrifuged. The resulting supernatants were precipitated with acetone, followed by SDS-PAGE (FIG. 3). FIG. 3 is an electrophoresis image showing the results of SDS-PAGE of beta-glucosidase expressed in 24 transformants that were prepared by introduction of SfBGL1 and the translational fusion partners into the Y2805Δgal80 strain. As shown in FIG. 3, it was found that beta-glucosidases having different sizes were expressed in the Y2805Δgal80 strain, as in the Y2805 strain.

Figure 4:
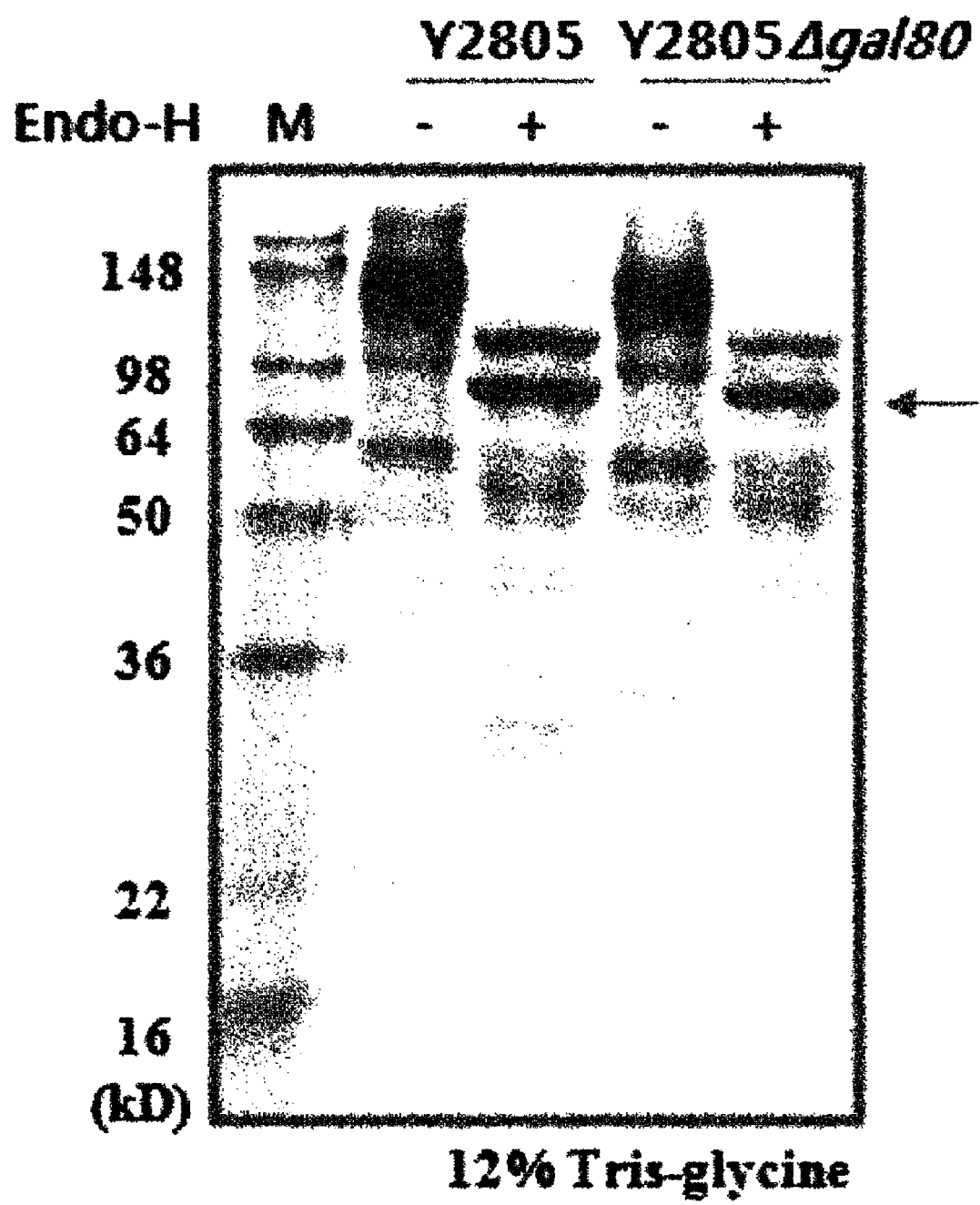
FIG. 4 is an electrophoresis image showing the results of SDS-PAGE after treatment of Endo-H enzyme for sugar chain analysis.

As in the analysis of Example 2, it was inferred that beta-glucosidases expressed in the Y2805Δgal80 strain were also those sugar-added by N-glycosylation. In order to confirm this, beta-glucosidase expressed in the transformant (Y2805Δgal80/ST19-SfBGL1) prepared by introduction of SfBGL1 and the TFPNO. 19 into Y2805Δgal80 was treated with Endo-H enzyme to remove sugars, and each of the deglycosylated samples was analyzed by SDS-PAGE (FIG. 4). FIG. 4 is an electrophoresis image showing the results of SDS-PAGE after treatment of beta-glucosidase expressed in the transformant derived from Y2805Δgal80 strain with Endo-H enzyme. As shown in FIG. 4, when beta-glucosidase expressed in each of the transformants was treated with Endo-H enzyme, its molecular weight was considerably reduced, indicating that the beta-glucosidases expressed in the transformants were N-glycosylated.

Example 3-2: Comparison of Beta-Glucosidase Activities in Mutated Y2805ΔGal80 Strains by pNPG Assay Each of the beta-glucosidases expressed in *Kluyveromyces marxianus* 7155, *Saccharomycopsis fibuligera*, the transformant prepared by introduction of YGaSW into Y2805Δgal80, and the transformants (Y2805Δgal80/ST15-SfBGL1, Y2805Δgal80/ST19-SfBGL1 and Y2805Δgal80/ST22-SfBGL1) prepared by introduction of SfBGL1 and the TFPNOs. 15, 19, and 22 into Y2805Δgal80 was subjected to pNPG assay to compare their enzymatic activities (Table 2).

TABLE 2

Beta-glucosidase activity in each expression strain

| Strain | Beta-glucosidase activity (U/ml) |
|---|---|
| K. marxianus 7155 | 10 |
| S. fibuligera | 26 |
| Y2805Δgal80/YGaSW | 25 |
| Y2805Δgal80/ST15-SfBGL1 | 293 |
| Y2805Δgal80/ST19-SfBGL1 | 1315 |
| Y2805Δgal80/ST22-SfBGL1 | 1275 |

As shown in Table 2, it was found that the transformant (Y2805Δgal80/ST19-SfBGL1) prepared by introduction of SfBGL1 and the TFPNO. 19 into Y2805Δgal80 expressed beta-glucosidase having the most excellent activity.

Example 3-3: Comparison of Beta-Glucosidase Activities in Mutated Y2805ΔGal80 Strains by EGDA (Esculin Gel Diffusion Assay)

Figure 5:
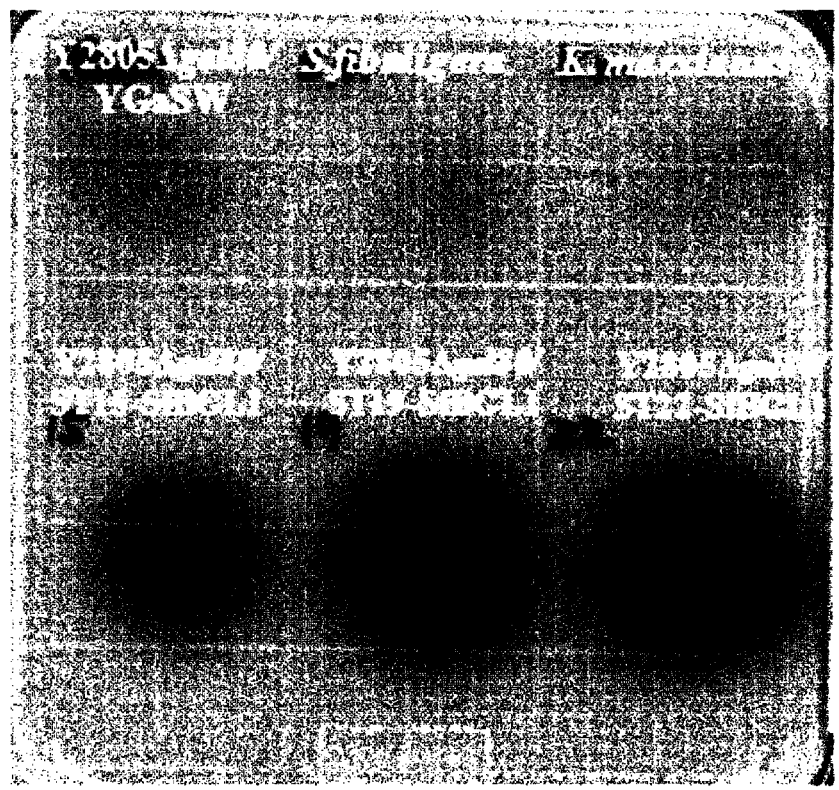
FIG. 5 is an image showing the results of analyzing the beta-glucosidase activity on the EGDA (Esculin Gel Diffusion Assay) plate media containing esculin.

Each 75 μl of the culture supernatants obtained by centrifugation of the strains used in Example 3-2 was coated to EGDA (Esculin Gel Diffusion Assay) plate media containing esculin (Esculin Gel Diffusion Assay: 0.2 M sodium citrate buffer (pH 6), 0.2% esculin), and reacted at 37° C. for 3 hours to examine the activity of beta-glucosidase expressed in each strain (FIG. 5). FIG. 5 is an electrophoresis image showing the results of analyzing the activities of the beta-glucosidases expressed in *Kluyveromyces marxianus* 7155, *Saccharomycopsis fibuligera*, the transformant prepared by introduction of YGaSW into Y2805Δgal80, and the transformants prepared by introduction of SfBGL1 and the TFPNOs. 15, 19, and 22 into Y2805Δgal80 on the EGDA plate media containing esculin. As shown in FIG. 5, when the culture supernatant obtained from the transformant (Y2805Δgal80/ST19-SfBGL1) prepared by introduction of SfBGL1 and the TFPNO. 19 into Y2805Δgal80 was reacted, the largest circle was found to be formed, indicating that the beta-glucosidase expressed in the Y2805Δgal80/ST19-SfBGL1 strain had the most excellent activity, which is consistent with the result of pNPG assay.

Figure 6:
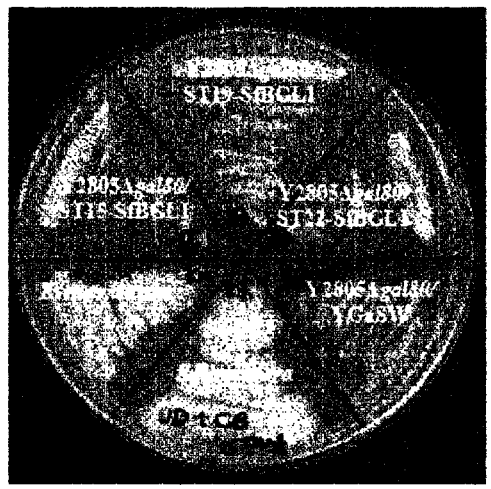
FIG. 6 is an image showing the results of culturing three transformant strains, *Kluyveromyces marxianus* 7155, *Saccharomyces cerevisiae* introduced with YGaSW, and *Saccharomycopsis fiburigera* in the cellobiose media.
Figure 6:
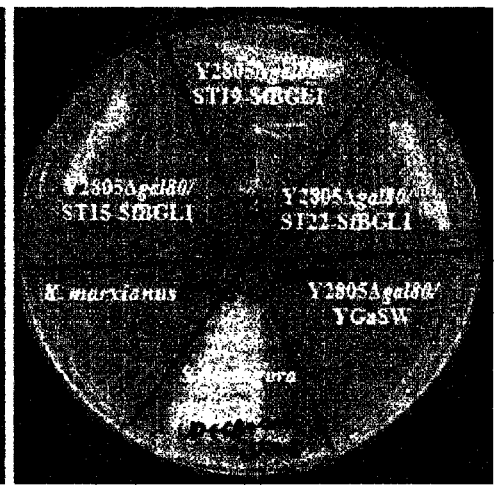

Example 3-4: Comparison of Growth in Mutated Y2805ΔGal80 Strains by Use of Cellobiose Each of the strains used in Example 3-2 was seeded on a UD plate media (0.67% amino acid-deficient yeast substrate, 0.77% uracil-deficient nutritional supplements and 2% glucose) containing cellobiose, and cultured at 30° C. for 2 days to compare growth between the strains. Each of the same strains was seeded on the UD plate media containing 1 μg/ml of antimycin A and cellobiose, and cultured at 30° C. for 6 days to compare growth between the strains (FIG. 6). FIG. 6 is an image showing the results of culturing *Kluyveromyces marxianus* 7155, *Saccharomycopsis fibuligera*, the transformant prepared by introduction of YGaSW into Y2805Δgal80, and the transformants prepared by introduction of SfBGL1 and the TFPNOs. 15, 19, and 22 into Y2805Δgal80 on the UD plate media containing cellobiose. As shown in FIG. 6, no growth difference in the strains was observed when antimycin A was not treated (left). In contrast, the transformant (Y2805Δgal80/ST19-SfBGL1) prepared by introduction of SfBGL1 and the TFP NO. 19 into Y2805Δgal80 showed relatively rapid growth when antimycin A was added (right).

Example 4: Comparison of Expression Level and Activity of Beta-Glucosidase According to TFPs It was examined whether beta-glucosidases show equivalent levels of expression and activity even though other TFPs are used instead of the foreign TFP (ST19) used in Examples 2 and 3.

First, PCR (1 cycle of 94° C. for 5 minutes; 25 cycles of 94° C. for 30 seconds, 55° C. for 30 seconds, 72° C. for 2 minutes, 72° C. for 1 minute; 1 cycle of 72° C. for 7 minutes) was performed using the genomic DNA of *Saccharomycopsis fibuligera* as a template and primer H574 (SEQ ID NO. 1) and antisense primer H576 (SEQ ID NO. 2) so as to obtain a *Saccharomycopsis fibuligera*-derived TFP fragment (own signal) being approximately 2 kb in size.

The *Saccharomycopsis fibuligera*-derived TFP fragment thus obtained was cleaved with restriction enzymes EcoRI and PstI, and introduced into the beta-glucosidase expression vector (YGaSfBGL1) prepared in Example 2 so as to prepare an expression vector including its own signal and SfBGL1. The expression vector was introduced into *Escherichia coli* DH5α to prepare a transformant. Subsequently, the transformant was cultured and a large amount of the expression vector was obtained therefrom. The expression vector thus obtained was introduced into Y2805Δgal80 strain to select single colonies expressing the *Saccharomycopsis fiburigera*-derived TFP and beta-glucosidase.

Next, in order to use MFα (mating factor alpha) signal, the same strain was transformed with the vector including ST6 corresponding to MFα among 24 types of the TFPs so as to obtain a transformant.

Figure 7:
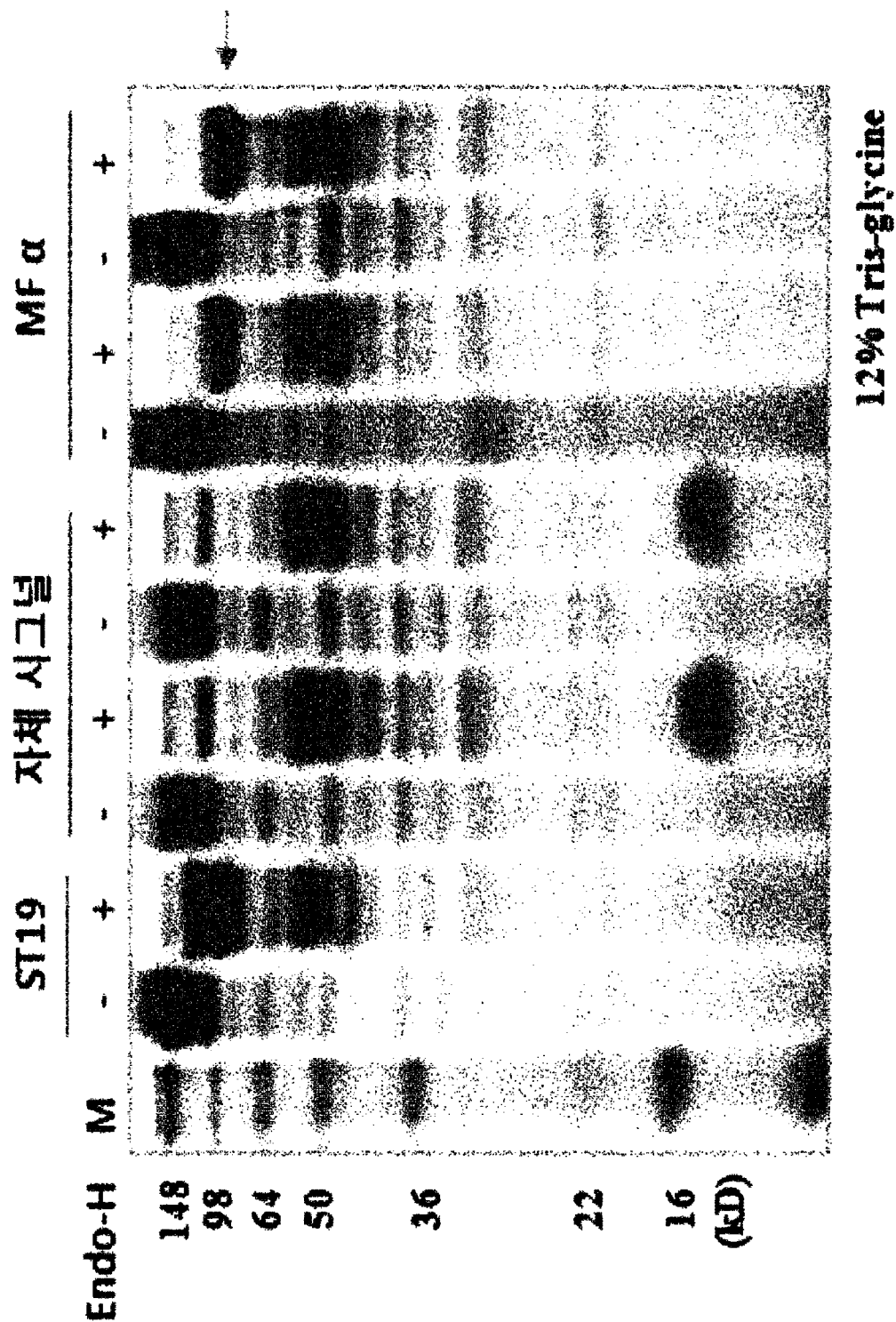
FIG. 7 is an electrophoresis image showing the results of SDS-PAGE after treatment of Endo-H for sugar chain analysis of the strains using its own secretion signal, MFα, or TFP19 as translational fusion partners.

The mutated Y2805Δgal80 strain including the foreign TFP (ST19) used in Examples 2 and 3, the above mutated Y2805Δgal80 strain including the *Saccharomycopsis fiburigera*-derived TFP and the mutated Y2805Δgal80 strain including MFα (mating factor alpha) signal were cultured in the YPD (1% yeast extract, 2% peptone and 2% glucose) media for 40 hours to express beta-glucosidase. Each strain thus cultured was centrifuged to obtain the culture supernatants including beta-glucosidase. Acetone was added to these culture supernatants to precipitate beta-glucosidase, and the precipitated beta-glucosidase was treated with (+) or without (−) Endo-H, followed by 12% SDS-PAGE (FIG. 7). FIG. 7 is an electrophoresis image showing the results of SDS-PAGE after treatment of beta-glucosidases expressed by using different TFPs with (+) or without (−) Endo-H. As shown in FIG. 7, it was found that the relatively large amount of beta-glucosidase could be expressed by use of the foreign TFP (ST19 or MFα signal), compared to the use of *Saccharomycopsis fiburigera*-derived TFP (own signal).

Moreover, beta-glucosidase expressed from each strain was subjected to pNPG assay to compare the beta-glucosidase activities (Table 3).

TABLE 3

Analysis of beta-glucosidase activity of each strain

|  |  | Beta-glucosidase activity (U/ml) |
|---|---|---|
| ST19 | 1 | 1127 |
| Own signal | 1 | 253 |
|  | 2 | 230 |
| MFα | 1 | 561 |
|  | 2 | 582 |

As shown in Table 3, it was found that beta-glucosidase activity was improved by use of ST19 as the TFP, compared to the use of other TFP (own signal or MFα signal).

Figure 8:
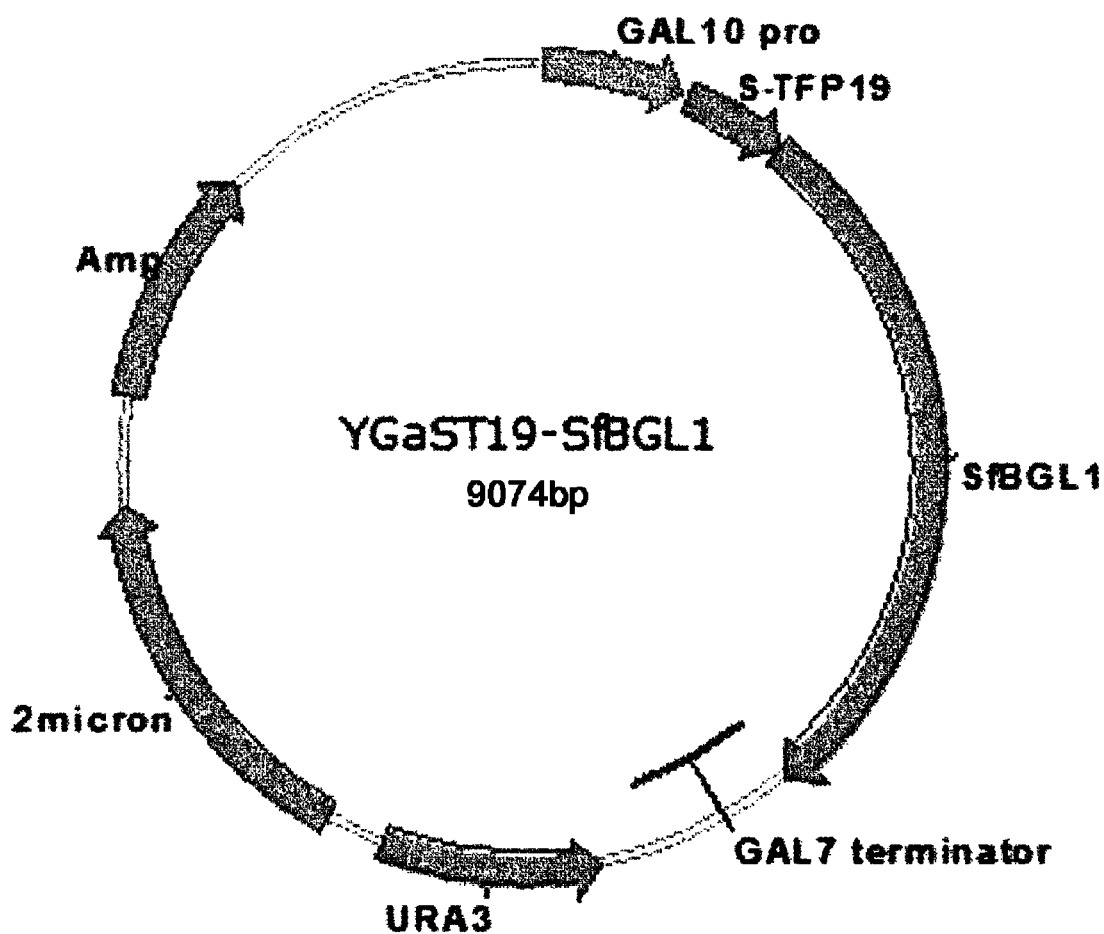
FIG. 8 is a diagram showing the plasmid pYGaST19-SfBGL1 finally selected.

Accordingly, the present inventors designated the beta-glucosidase expression vector including the TFP ST19 and *Saccharomycopsis fiburigera*-derived beta-glucosidase gene SfBGL1 as "pYGaST19-SfBGL1" (FIG. 8). FIG. 8 is a schematic map of the beta-glucosidase expression vector pYGaST19-SfBGL1, which includes the TFP ST19 and *Saccharomycopsis fiburigera*-derived beta-glucosidase gene SfBGL1.

Example 5: Development of Beta-Glucosidase Having Enhanced Activity

Example 5-1: Preparation of Mutant Libraries Capable of Expressing Beta-Glucosidase In order to screen SfBGL1 having enhanced activity, error-prone PCR was performed to prepare mutant libraries. That is, error-prone PCR was performed using the beta-glucosidase expression vector pYGaST19-SfBGL1 determined in Example 4 as a template and GAL47 (SEQ ID NO. 7) and GT50R primers (SEQ ID NO. 6) and a PCR random mutagenesis kit (Clontech). At this time, the mutagenesis was performed to induce 2 mutations per 1 kb according to instructions included in the kit under the conditions of 1 cycle of 94° C. for 30 seconds; 25 cycles of 94° C. for 30 seconds, 68° C. for 3 minutes; 1 cycle of 68° C. for 1 minute.

GAL47:

(SEQ ID NO. 7)
5'-gcgtccatccaaaaaaaaagtaagaattttttgaaaattcaagaat tc-3'

The fragment resulting from error-prone PCR was cloned into an YGa vector to prepare a mutant library.

Example 5-2: Preparation of Mutants Capable of Expressing Beta-Glucosidase Having Enhanced Activity The prepared mutant library was introduced into *Saccharomyces cerevisiae* Y2805Δgal1 (Mat a pep4::HIS3 Gal1::Tcl90, prb1 can1 his3-200 ura3-52) strain which require small amount of galactose for induction of GAL promoter to obtain transformants. The transformants thus obtained were seeded on YNB-CB-gal-A (0.67% amino acid-deficient yeast substrate, 0.77% uracil-deficient nutritional supplements, 2% cellobiose, 0.3% galactose, 1 μg/ml antimycin A) plate media to obtain approximately 200 colonies. Each transformant was obtained from the colonies, and beta-glucosidase expressed in each transformant was subjected to EGDA and pNPG assays to compare beta-glucosidase activity between the wild-type pYGaST19-SfBGL1 and the transformants (A and B of FIG. 9). A of FIG. 9 is an image showing the result of EGDA assay of beta-glucosidase expressed in the transformants that were prepared using the mutant library, and B of FIG. 9 is an image showing the result of pNPG assay of beta-glucosidase expressed in the transformants that were prepared using the mutant library. As shown in FIG. 9, 15 transformants capable of expressing beta-glucosidase having more increased activity than beta-glucosidase expressed in the wild-type pYGaST19-SfBGL1 were selected. Among the selected transformants, 3 transformants (NOs. 10, 12 and 14) were found to express beta-glucosidase having approximately 30% higher activity than that of beta-glucosidase expressed in the wild-type pYGaST19-SfBGL1.

Example 5-3: Structural Analysis of Beta-Glucosidase Having Enhanced Activity

Figure 10:
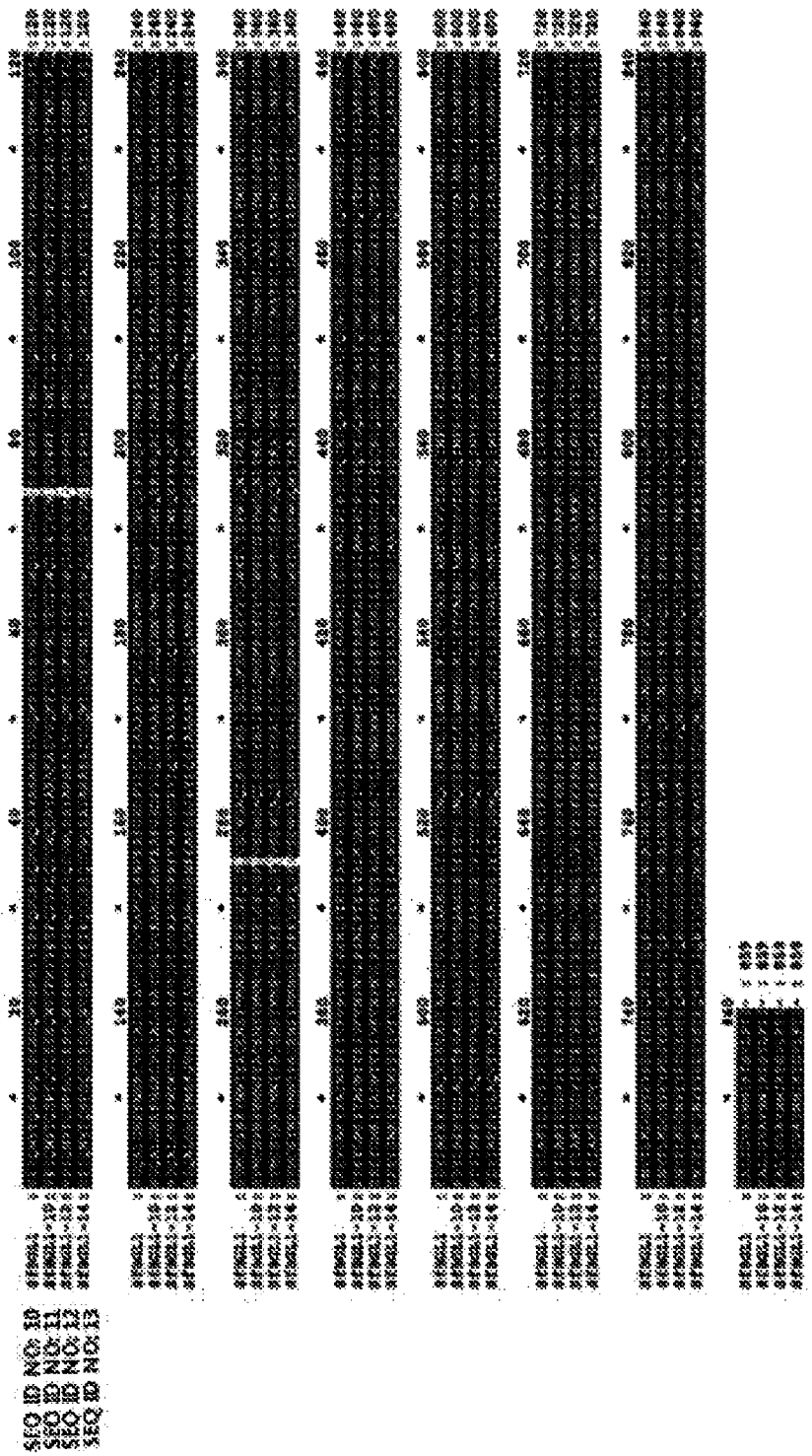
FIG. 10 is a diagram showing the results of comparing the protein sequences between the wild-type (wt) SfBGL1 (SEQ ID NO: 10) and the mutant SfBGL1 (SEQ ID NOS 11-13, respectively, in order of appearance)

The result of analyzing the sequence of the mutated SfBGL1 included in 3 transformants (NOs. 10, 12 and 14) capable of expressing beta-glucosidase having approximately 30% higher activity than that of beta-glucosidase expressed in the wild-type pYGaST19-SfBGL1 which was obtained in Example 5-2 showed that the mutated SfBGL1 did not show common characteristics (FIG. 10). FIG. 10 is a diagram showing the results of comparing the amino acid sequences between the wild-type beta-glucosidase and mutated beta-glucosidase. As shown in FIG. 10, the transformant NO. 10 was found to include a polynucleotide (SEQ ID NO. 9) having 4 mutated nucleotides (A114G, T1377C, T1527A, T2251C) without mutations in the amino acids of beta-glucosidase, the transformant NO. 12 was found to include a mutation (T74A) of threonine (T) to alanine (A) at position 74 of the amino acid sequence of beta-glucosidase (SEQ ID NO: 12), and the transformant NO. 14 was found to include a mutation (V275A) of valine (V) to alanine (A) at position 275 of the amino acid sequence of beta-glucosidase (SEQ ID NO 13).

Example 5-4: Combination of Beta-Glucosidase Mutations

It was examined whether the beta-glucosidase activity can be further enhanced by combinations of the mutations examined in Example 5-3.

To this end, the transformant (Y2805Δgal80/ST19-SfBGL1) introduced with the wild-type SfBGL1, the transformant NO. 10 (Y2805Δgal80/ST19-SfBGL1-10), the transformant (Y2805Δgal80/ST19-SfBGL1-12) prepared by introduction of T74A mutation into the mutated SfBGL1 of the transformant NO. 10, and the transformant (Y2805Δgal80/ST19-SfBGL1-14) prepared by introduction of T74A and V275A mutations into the mutated SfBGL1 of the transformant NO. 10 were prepared, and beta-glucosidase activities of these transformants were determined and compared by pNPG assay (Table 4).

TABLE 4

Comparison of beta-glucosidase activities between transformants

| Transformant | Beta-glucosidase activity (U/ml) |
| --- | --- |
| Y2805Δgal80/ST19-SfBGL1 | 1510 |
| Y2805Δgal80/ST19-SfBGL1-10 | 1928 |
| Y2805Δgal80/ST19-SfBGL1-12 | 2050 |
| Y2805Δgal80/ST19-SfBGL1-14 | 2063 |

As shown in Table 4, it was found that the transformant prepared by introduction of T74A mutation into the mutated SfBGL1 of the transformant NO. 10 expressed beta-glucosidase having more enhanced activity, and the transformant prepared by introduction of T74A and V275A mutations into the mutated SfBGL1 of the transformant NO. 10 expressed beta-glucosidase having the most excellent activity.

Example 6: Mass-Production of Beta-Glucosidase

Mass-production of beta-glucosidase was performed using the transformant (Y2805Δgal80/ST19-SfBGL1-10) for producing the mutated beta-glucosidase prepared in Example 5-4.

First, the transformant (Y2805Δgal80/ST19-SfBGL1-10) was primary cultured in 50 ml of a minimal liquid medium (0.67% amino acid-deficient yeast substrate, 0.5% casamino acid and 2% glucose), and then cultured in 200 ml of YPD medium to activate beta-glucosidase expression.

The transformant (Y2805Δgal80/ST19-SfBGL1-10), of which beta-glucosidase expression was activated, was seeded in the YPD medium and cultured at 30° C. for 48 hours by fed batch culture. The volume of primary culture medium was 2 L. 12 hours after cultivation, additional glucose was added at an average rate of 0.2 g/hr, and the final volume reached 2.5 L upon termination. After completing the cultivation, the culture was centrifuged to obtain a culture supernatant, and beta-glucosidase included in the culture supernatant was concentrated using 50 mM Tris buffer (pH 7.5) by ultrafiltration (molecular weight cut-off: 30,000).

Figure 11A:
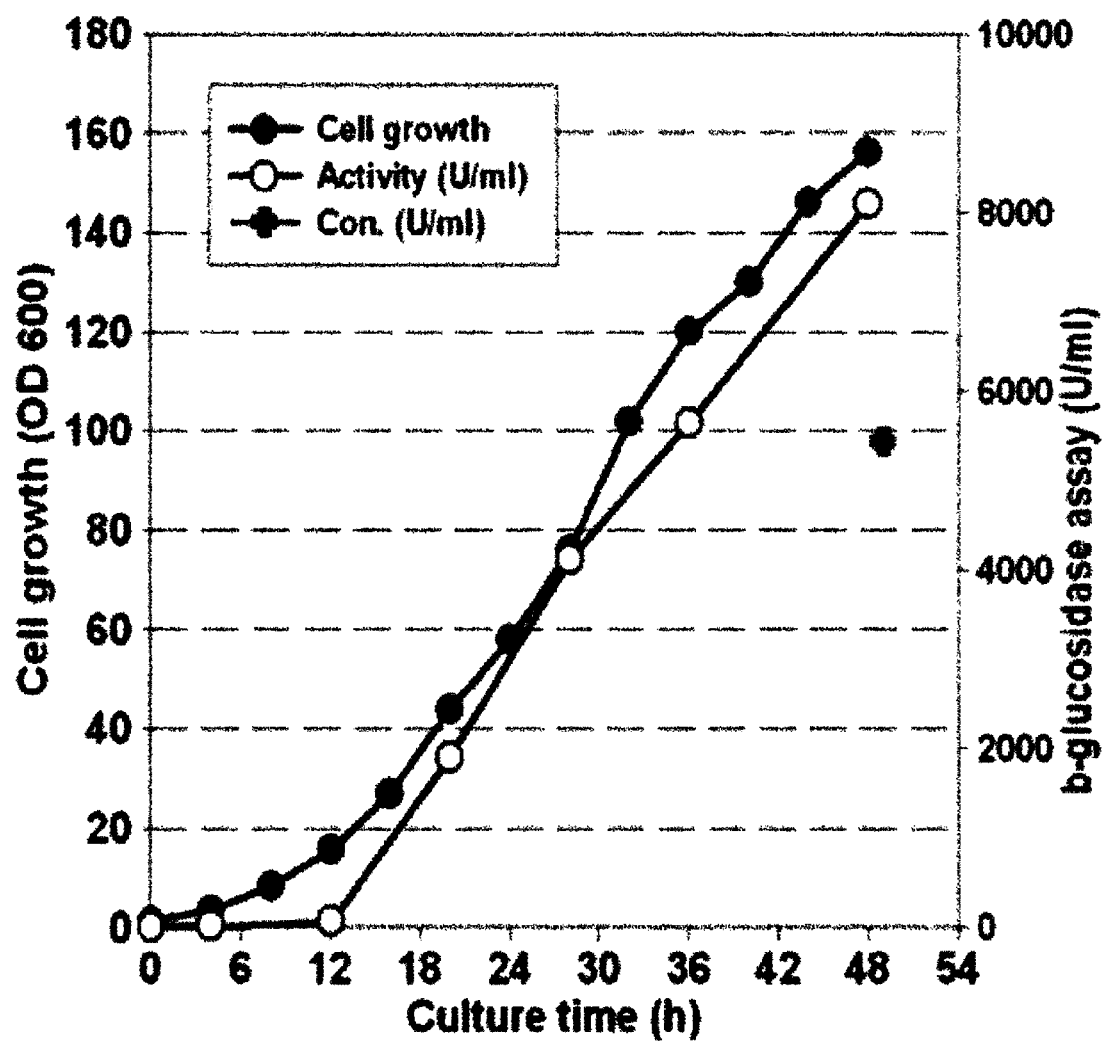
FIG. 11a is a graph showing the growth of the transformant (Y2805Δgal80/ST19-SfBGL1-10) and the activity of the mutated beta-glucosidase produced therefrom over cultivation time.

During the cultivation time, a part of the culture was collected as a sample over time, and the growth (OD 600) and change in beta-glucosidase activity (U/ml) of the transformant were compared over cultivation time (FIG. 11a). FIG. 11a is a graph showing the growth of the transformant (Y2805Δgal80/ST19-SfBGL1-10) and change in the activity of the mutated beta-glucosidase produced therefrom over cultivation time. As shown in FIG. 11a, it was found that both of the growth (OD 600) and the beta-glucosidase activity (U/ml) of the transformant were increased over time. After 48 hr-cultivation, beta-glucosidase was secreted into the medium at a concentration of approximately 2 g/l, and the total activity of the produced beta-glucosidase was approximately 8000 units.

Figure 11B:
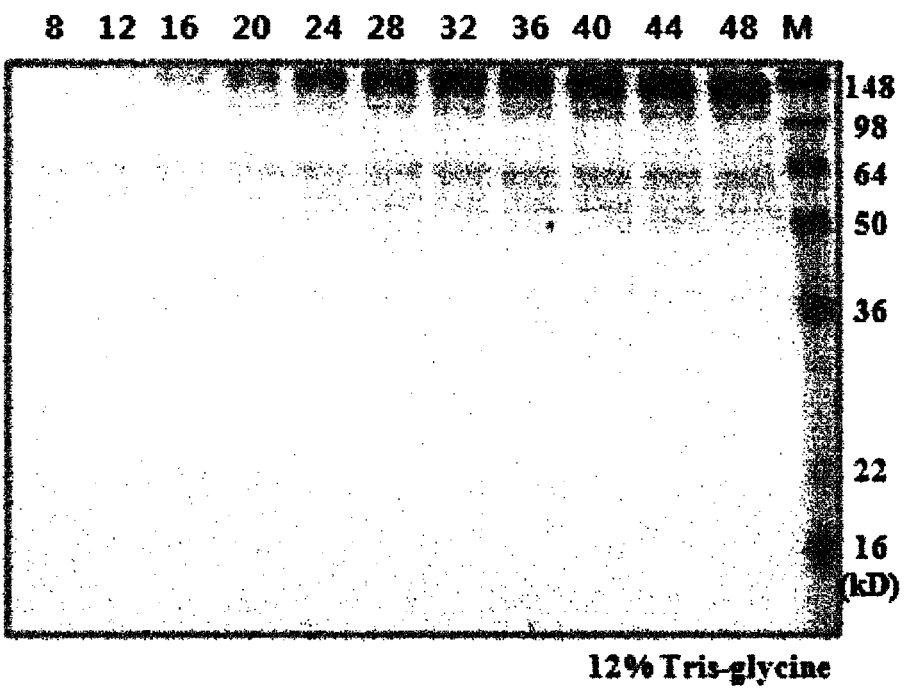
FIG. 11b is an electrophoresis image showing the content of beta-glucosidase that was secreted from the transformant (Y2805Δgal80/ST19-SfBGL1-10) into the culture medium over cultivation time.

Further, a part of the culture was collected as a sample over the cultivation time (8, 12, 16, 20, 24, 28, 32, 36, 40, 44 and 48 hours after cultivation), and beta-glucosidase included therein was analyzed by 12% SDS-PAGE (FIG. 11b). FIG. 11b is an electrophoresis image showing the content of beta-glucosidase that was secreted from the transformant (Y2805Δgal80/ST19-SfBGL1-10) into the culture medium over the cultivation time. As shown in B of FIG. 11, it was found that the content of beta-glucosidase secreted into the culture medium was increased over the cultivation time.

Example 7: Production of Ethanol by Use of Beta-Glucosidase

It was examined whether ethanol can be produced from a cellulose-based agricultural biomass and a seaweed-derived biomass, such as palm fruit by-products (empty fruit bunch, EFB), Jerusalem artichokes tuber and Gelidium cellulose as well as glucose, cellobiose, and alpha-cellulose using the transformant expressing beta-glucosidase.

Example 7-1: Production of Ethanol by Use of Glucose as Substrate

Figure 12A:
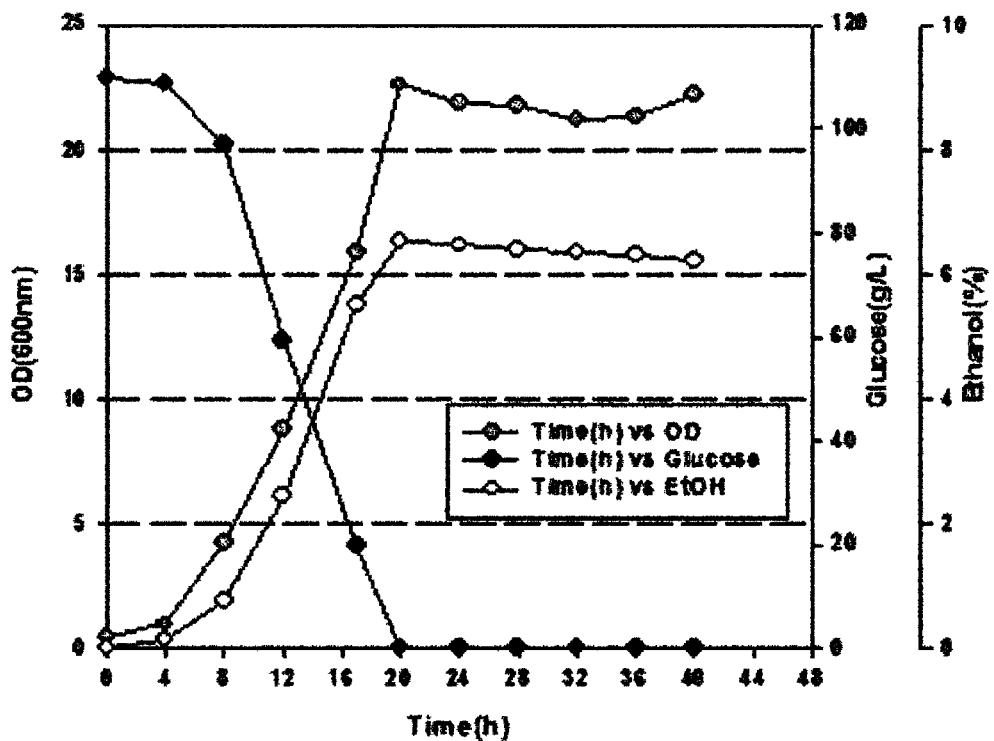
FIG. 12a is a graph showing the growth of the transformant, and changes in the glucose and ethanol concentrations in the medium over cultivation time when ethanol was produced by the transformant (Y2805Δgal80/ST19-SfBGL1-10) expressing the mutated beta-glucosidase in the medium containing glucose as a substrate.

The transformant (Y2805Δgal80/ST19-SfBGL1-10) used in Example 6 was primary cultured in 50 ml of a minimal liquid medium, and then cultured in 200 ml of YPD medium. Then, the culture was seeded on a culture medium for ethanol production containing 10% glucose as a substrate (0.5% yeast extract, 0.5% peptone, 0.5% potassium phosphate anhydrous, 0.2% ammonium sulfate, 0.06% magnesium sulfate, pH 5.0), and cultured by batch culture under ethanol fermentation conditions (30° C., 40 hours, RPM 100 and aeration 0.1~2 vvm) (FIG. 12a). FIG. 12a is a graph showing the growth of the transformant, and changes in the glucose and ethanol concentrations in the medium over cultivation time when ethanol was produced by culturing the transformant (Y2805gal80/ST19-SfBGL1-10) expressing the mutated beta-glucosidase in the medium containing glucose as a substrate. As shown in FIG. 12a, glucose consumption began at 4 hours after cultivation, and glucose in the medium was completely consumed at 20 hours after cultivation, and approximately 6% ethanol was produced.

Example 7-2: Production of Ethanol by Use of Cellobiose as Substrate

Ethanol was produced using a medium containing cellobiose as a substrate, which can be degraded into glucose by beta-glucosidase.

Figure 12B:
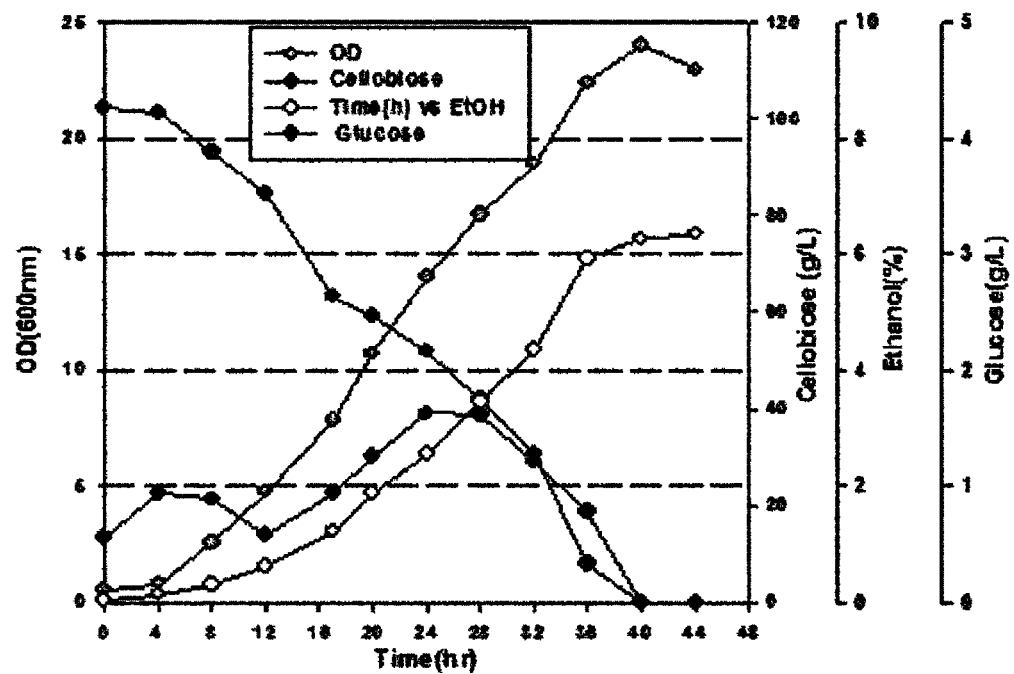
FIG. 12b is a graph showing the growth of the transformant and changes in the glucose and ethanol concentrations in the medium over cultivation time when ethanol was produced by the transformant (Y2805Δgal80/ST19-SfBGL1-10) expressing the mutated beta-glucosidase in the medium containing cellobiose as a substrate.

That is, ethanol was produced in the same manner as in Example 7-1, except for using a culture medium for ethanol production containing 100 g/l cellobiose as a substrate and 0.5 g/l glucose as a carbon source (FIG. 12b). FIG. 12b is a graph showing the growth of the transformant and changes in the glucose and ethanol concentrations in the medium over cultivation time when ethanol was produced by culturing the transformant (Y2805Δgal80/ST19-SfBGL1-10) expressing the mutated beta-glucosidase in the medium containing cellobiose as a substrate. As shown in FIG. 12b, the glucose concentration in the medium slightly increased by degradation of cellobiose immediately after cultivation. However, both glucose and cellobiose in the medium were reduced in the same level at 24 hours after cultivation, and both glucose and cellobiose in the medium were completely consumed at 40 hours after cultivation, resulting in production of approximately 6% ethanol.

Example 7-3: Production of Ethanol by Use of Alpha-Cellulose as Substrate

Because alpha-cellulose is degraded into cellobiose by cellulase, and cellobiose is degraded into glucose by beta-glucosidase, it was intended to produce ethanol using a medium containing alpha-cellulose as a substrate.

Example 7-3-1: Production of Ethanol by Use of 10 FPU/g of Cellulase

Figure 13A:
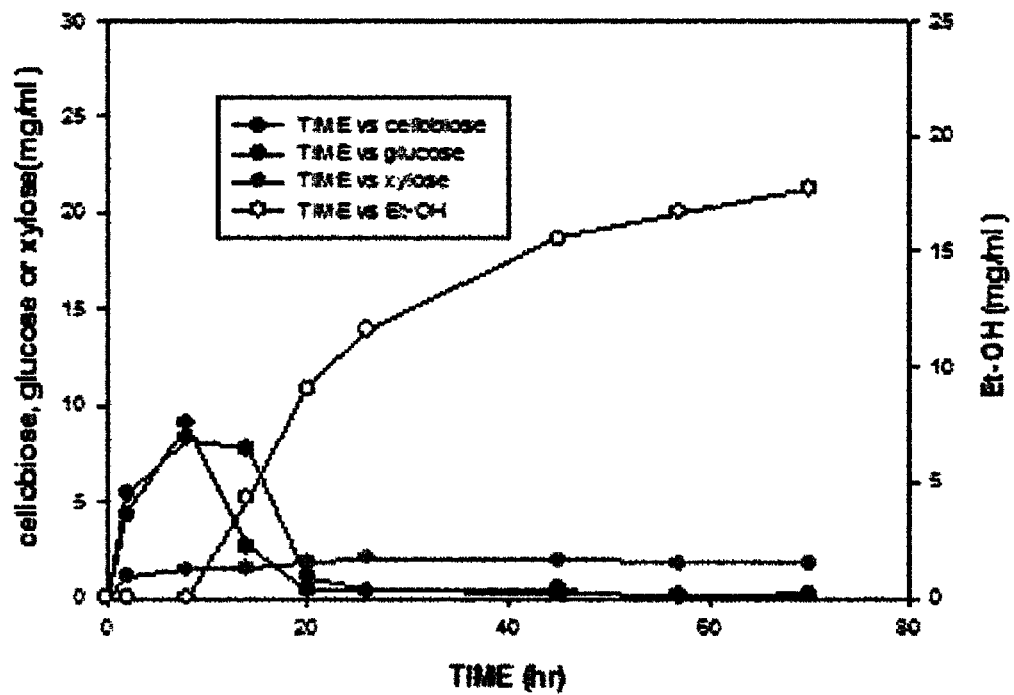
FIG. 13a is a graph showing changes in the cellobiose, Glucose, xylose and ethanol concentrations in the medium over cultivation time when ethanol was produced by the transformant (Y2805Δgal80/ST19-SfBGL1-10) expressing the mutant beta-glucosidase in the medium containing α-cellulose as a substrate under treatment of 10 FPU/g of cellulose.

The transformant (Y2805Δgal80/ST19-SfBGL1-10) used in Example 6 was primary cultured in 50 ml of a minimal liquid medium, and then cultured in 200 ml of YPD medium. Then, the culture was seeded on a culture medium for ethanol production containing 10% α-cellulose as a substrate and 10 FPU (filter paper unit)/g of cellulase (celluclast 1.5 l, Novozyme) to perform saccharification (8 hours, 50° C., RPM 300), and cultured under ethanol fermentation conditions (30° C., 70 hours, RPM 100~300 and aeration 0.1~2 vvm) (FIG. 13a). FIG. 13a is a graph showing changes in the cellobiose, glucose, xylose and ethanol concentrations in the medium over cultivation time when ethanol was produced by culturing the transformant (Y2805Δgal80/ST19-SfBGL1-10) expressing the mutated beta-glucosidase in the medium containing α-cellulose as a substrate under treatment of 10 FPU/g of cellulase. As shown in FIG. 13a, the glucose and cellobiose concentrations increased after cultivation, but decreased after a predetermined time. When the glucose and cellobiose concentrations began to decrease, ethanol was produced, and the ethanol concentration continuously increased. When the cultivation was completed, 17.5 g/l of ethanol was produced.

Figure 13B:
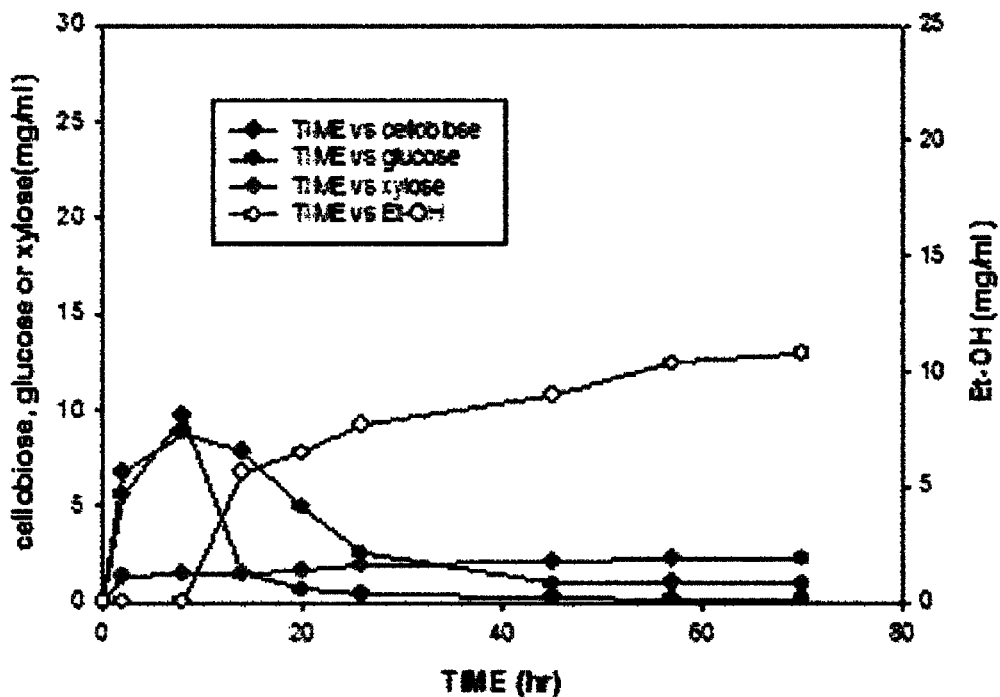
FIG. 13b is a graph showing changes in the cellobiose, glucose, xylose and ethanol concentrations in the medium over cultivation time when ethanol was produced by the control strain (Y2805Δgal80/YGaSW) introduced with only the vector in the medium containing α-cellulose as a substrate under treatment of 10 FPU/g of cellulase.

Meanwhile, the experiment was performed in the same manner as above, except that a host cell (Y2805Δgal80) was used as a control group instead of the transformant (Y2805Δgal80/ST19-SfBGL1-10) (FIG. 13b). FIG. 13b is a graph showing changes in the cellobiose, glucose, xylose and ethanol concentrations in the medium over cultivation time when ethanol was produced by culturing the control strain (Y2805Δgal80/YGaSW) introduced with only the vector in the medium containing α-cellulose as a substrate under treatment of 10 FPU/g of cellulase. As shown in FIG. 13b, the glucose and cellobiose concentrations increased after cultivation, but decreased after a predetermined time. When the glucose and cellobiose concentrations began to decrease, ethanol was produced, and the ethanol concentration continuously increased. When the cultivation was completed, 11 g/l of ethanol was produced.

As shown in FIGS. 13a and 13b, when the transformant (Y2805/gal80/ST19-SfBGL1-10) introduced with the mutated beta-glucosidase gene provided by the present invention was used, ethanol productivity was increased to approximately 35%.

Example 7-3-2: Production of Ethanol by Use of 5 FPU/g of Cellulase

Figure 14A:
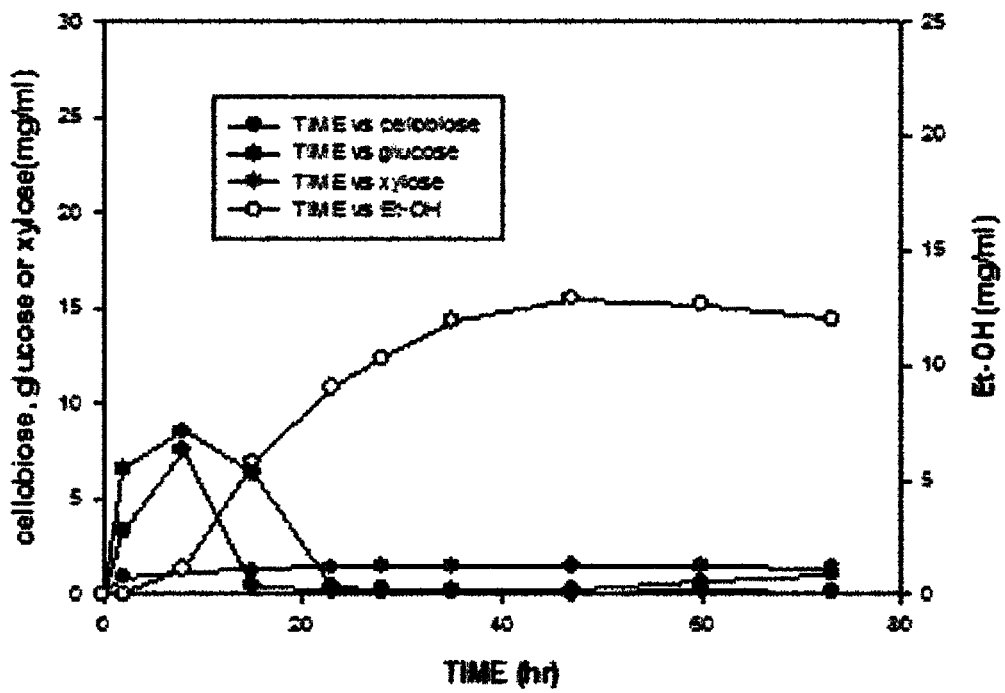
FIG. 14a is a graph showing changes in the cellobiose, glucose, xylose and ethanol concentrations in the medium over cultivation time when ethanol was produced by the transformant (Y2805Δgal80/ST19-SfBGL1-10) expressing the mutant beta-glucosidase in the medium containing α-cellulose as a substrate under treatment of 5 FPU/g of cellulase.
Figure 14B:
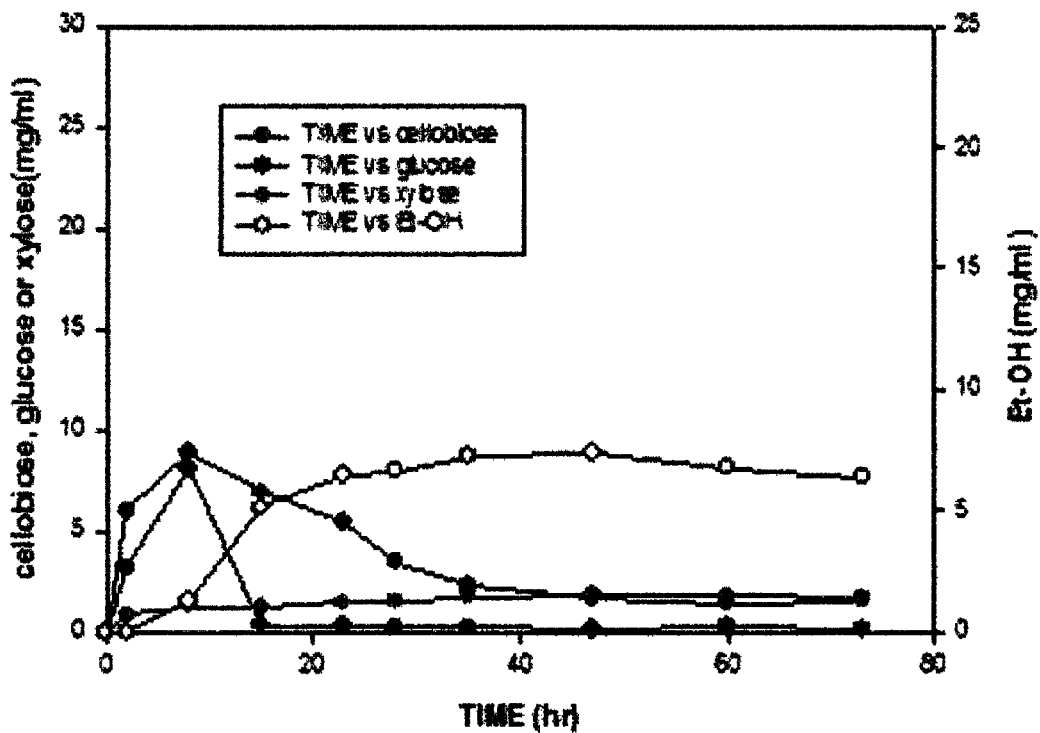
FIG. 14b is a graph showing changes in the cellobiose, glucose, xylose and ethanol concentrations in the medium over cultivation time when ethanol was produced by the control strain (Y2805Δgal80/YGaSW) introduced with only the vector in the medium containing α-cellulose as a substrate under treatment of 5 FPU/g of cellulase.

The experiment was performed in the same manner as in Example 7-3-1, except for using 5 FPU/g of cellulase instead of 10 FPU/g of cellulase (FIGS. 14a and 14b).

FIG. 14a is a graph showing changes in the cellobiose, glucose, xylose and ethanol concentrations in the medium over cultivation time when ethanol was produced by culturing the transformant (Y2805Δgal80/ST19-SfBGL1-10) expressing the mutated beta-glucosidase in the medium containing α-cellulose as a substrate under treatment of 5 FPU/g of cellulase. As shown in FIG. 14a, the glucose and cellobiose concentrations increased after cultivation, but decreased after a predetermined time. Ethanol was produced immediately after cultivation. The ethanol concentration continuously increased, but decreased after a predetermined time. When the cultivation was completed, approximately 12 g/l of ethanol was produced.

Meanwhile, FIG. 14b is a graph showing changes in the cellobiose, glucose, xylose and ethanol concentrations in the medium over cultivation time when ethanol was produced by culturing the control strain (Y2805Δgal80/YGaSW) introduced with only the vector in the medium containing α-cellulose as a substrate under treatment of 5 FPU/g of cellulase. As shown in FIG. 14b, the glucose and cellobiose concentrations increased after cultivation, but decreased after a predetermined time. Ethanol was produced immediately after cultivation. The ethanol concentration continuously increased, but decreased after a predetermined time. When the cultivation was completed, approximately 6 g/l of ethanol was produced.

As shown in FIGS. 14a and 14b, when a relatively small amount of cellulase was treated, ethanol productivity was increased to approximately 50% by using the transformant (Y2805Δgal80/ST19-SfBGL1-10) introduced with the mutated beta-glucosidase gene provided by the present invention, suggesting that sufficient ethanol production did not occur because the efficiency of converting the α-cellulose in the medium into cellobiose was low.

Example 7-4: Production of Ethanol by Use of Biomass as Substrate

It was intended to produce ethanol using media containing a cellulose-based agricultural biomass and a seaweed-derived biomass, such as palm fruit by-products (empty fruit bunch, EFB), Jerusalem artichokes tuber and Gelidium cellulose as a substrate.

Example 7-4-1: Production of Ethanol by Use of Palm Fruit By-Products as Substrate First, a 10-fold volume of 2% sodium hydroxide solution was added to palm fruit by-products (EFB), and a high temperature and high pressure reaction was performed at 120° C. for 1 hour. The resultant was washed, and neutralized with 1 M hydrochloric acid. The neutralized product was dried in a 60° C. dryer to a moisture content of approximately 10%, thereby obtain an EFB substrate.

Figure 15A:
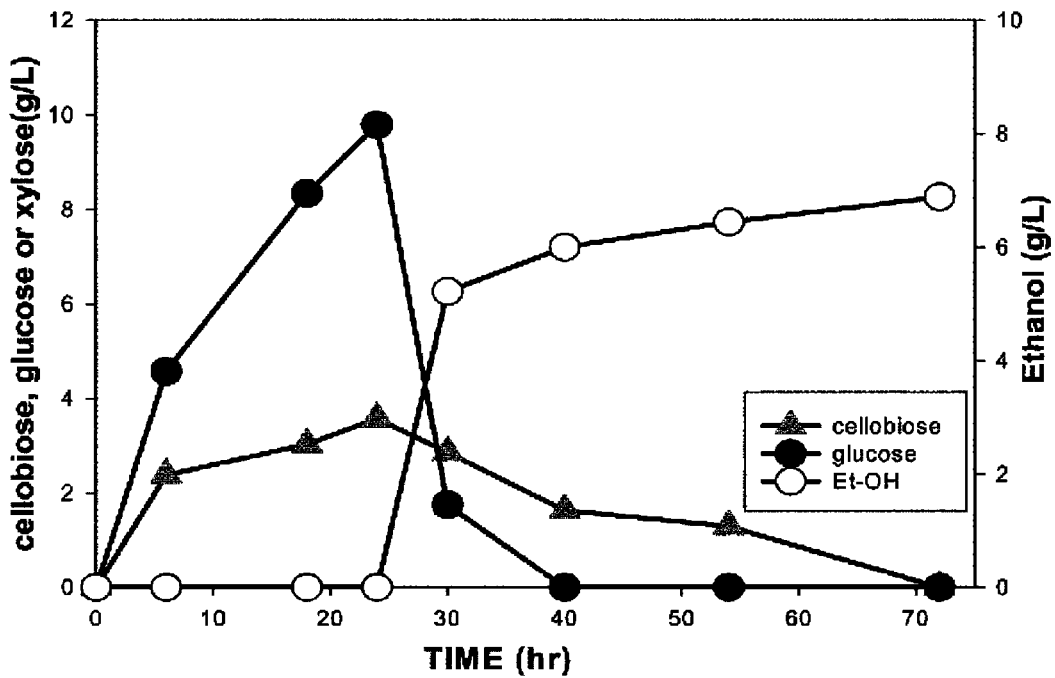
FIG. 15a is a graph showing changes in the cellobiose, glucose, and ethanol concentrations in the medium over cultivation time when ethanol was produced by the transformant (Y2805Δgal80/ST19-SfBGL1-10) expressing the mutant beta-glucosidase in the medium containing Empty Fruit Bunch (EFB) as a substrate under treatment of 5 FPU/g of cellulase.

Next, the transformant (Y2805Δgal80/ST19-SfBGL1-10) used in Example 6 was primary cultured in 50 ml of a minimal liquid medium, and then cultured in 200 ml of YPD medium. Then, the culture was seeded on a culture medium for ethanol production containing 10% EFB substrate as a substrate and 5 FPU/g of cellulase to perform saccharification (8 hours, 50° C., RPM 300), and cultured under ethanol fermentation conditions (30° C., 70 hours, RPM 100-300 and aeration 0.1~2 vvm) (FIG. 15a). FIG. 15a is a graph showing changes in the cellobiose, glucose, and ethanol concentrations in the medium over cultivation time when ethanol was produced by culturing the transformant (Y2805Δgal80/ST19-SfBGL1-10) expressing the mutated beta-glucosidase in the medium containing EFB as a substrate under treatment of 5 FPU/g of cellulase. As shown in FIG. 15a, the glucose and cellobiose concentrations increased after cultivation, but decreased after a predetermined time. When the glucose and cellobiose concentrations began to decrease, ethanol was produced, and the ethanol concentration continuously increased. When the cultivation was completed, approximately 9 g/l of ethanol was produced.

Figure 15B:
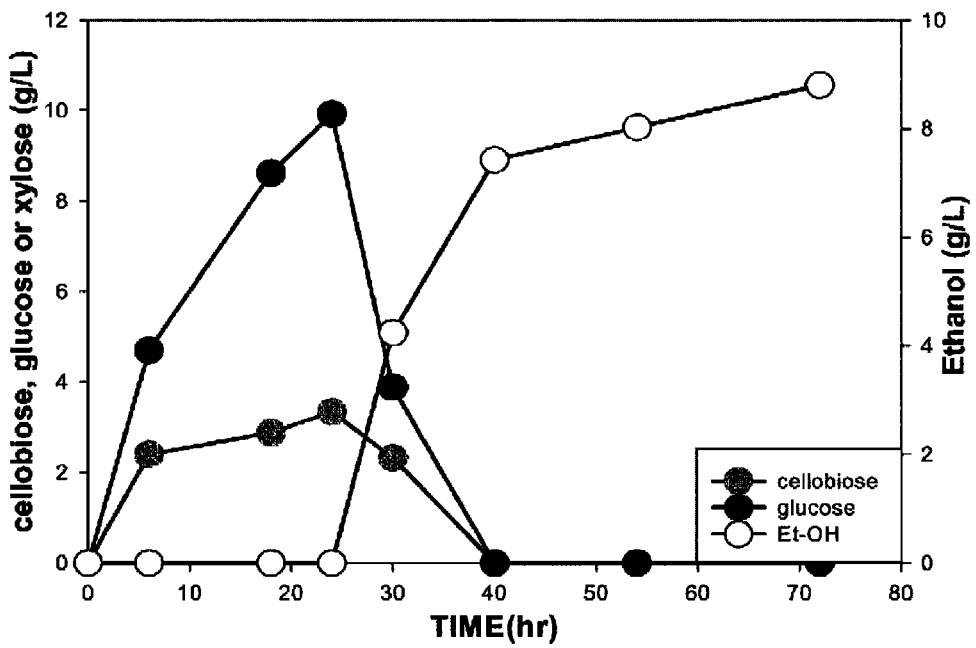
FIG. 15b is a graph showing changes in the cellobiose, glucose, and ethanol concentrations in the medium over cultivation time when ethanol was produced by culturing the control strain (Y2805Δgal80/YGaSW) introduced with only the vector in the medium containing EFB as a substrate under treatment of 5 FPU/g of cellulase.

Meanwhile, the experiment was performed in the same manner as above, except that a host cell (Y2805Δgal80) was used as a control group instead of the transformant (Y2805Δgal80/ST19-SfBGL1-10) (FIG. 15b). FIG. 15b is a graph showing changes in the cellobiose, glucose, and ethanol concentrations in the medium over cultivation time when ethanol was produced by culturing the control strain (Y2805Δgal80/YGaSW) introduced with only the vector in the medium containing EFB as a substrate under treatment of 5 FPU/g of cellulase. As shown in FIG. 15b, the glucose and cellobiose concentrations increased after cultivation, but decreased after a predetermined time. When the glucose and cellobiose concentrations began to decrease, ethanol was produced, and the ethanol concentration continuously increased. When the cultivation was completed, 7 g/l of ethanol was produced.

As shown in FIGS. 15a and 15b, when the transformant (Y2805Δgal80/ST19-SfBGL1-10) introduced with the mutated beta-glucosidase gene provided by the present invention was used, ethanol productivity was increased to approximately 33% even though the cellulose-based agricultural biomass, palm fruit by-product (empty fruit bunch, EFB) was used as a substrate, suggesting that the transformant introduced with the mutated beta-glucosidase gene provided by the present invention showed a remarkably high degradation rate of cellobiose in the medium, compared to the host cell used as a control group, resulting in the increased ethanol productivity.

Example 7-4-2: Production of Ethanol by Use of Jerusalem Artichokes Tuber as Substrate The experiment was performed in the same manner as in Example 7-4-1, except for using Jerusalem artichokes tuber instead of the cellulose-based agricultural biomass, palm fruit by-products (empty fruit bunch, EFB) (FIGS. 16a and 16b).

Figure 16A:
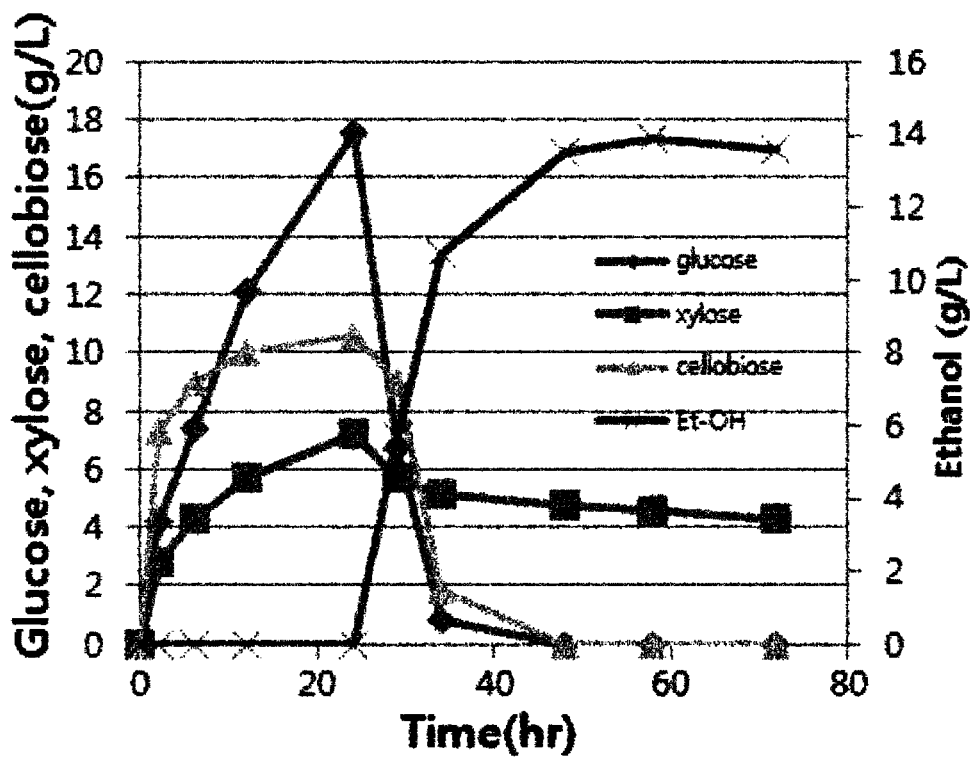
FIG. 16a is a graph showing changes in the cellobiose, xylose, glucose, and ethanol concentrations in the medium over cultivation time when ethanol was produced by culturing the transformant (Y2805Δgal80/ST19-SfBGL1-10) expressing the mutated beta-glucosidase in the medium containing Jerusalem artichokes tuber as a substrate under treatment of 5 FPU/g of cellulase.

FIG. 16a is a graph showing changes in the cellobiose, xylose, glucose, and ethanol concentrations in the medium over cultivation time when ethanol was produced by culturing the transformant (Y2805Δgal80/ST19-SfBGL1-10) expressing the mutated beta-glucosidase in the medium containing Jerusalem artichokes tuber as a substrate under treatment of 5 FPU/g of cellulase. As shown in FIG. 16a, the glucose, cellobiose, and xylose concentrations increased after cultivation, but decreased after a predetermined time. When the glucose, cellobiose and xylose concentrations began to decrease, ethanol was produced. The ethanol concentration continuously increased, but was maintained at a predetermined level after a predetermined time. When the cultivation was completed, approximately 14 g/l of ethanol was produced.

Figure 16B:
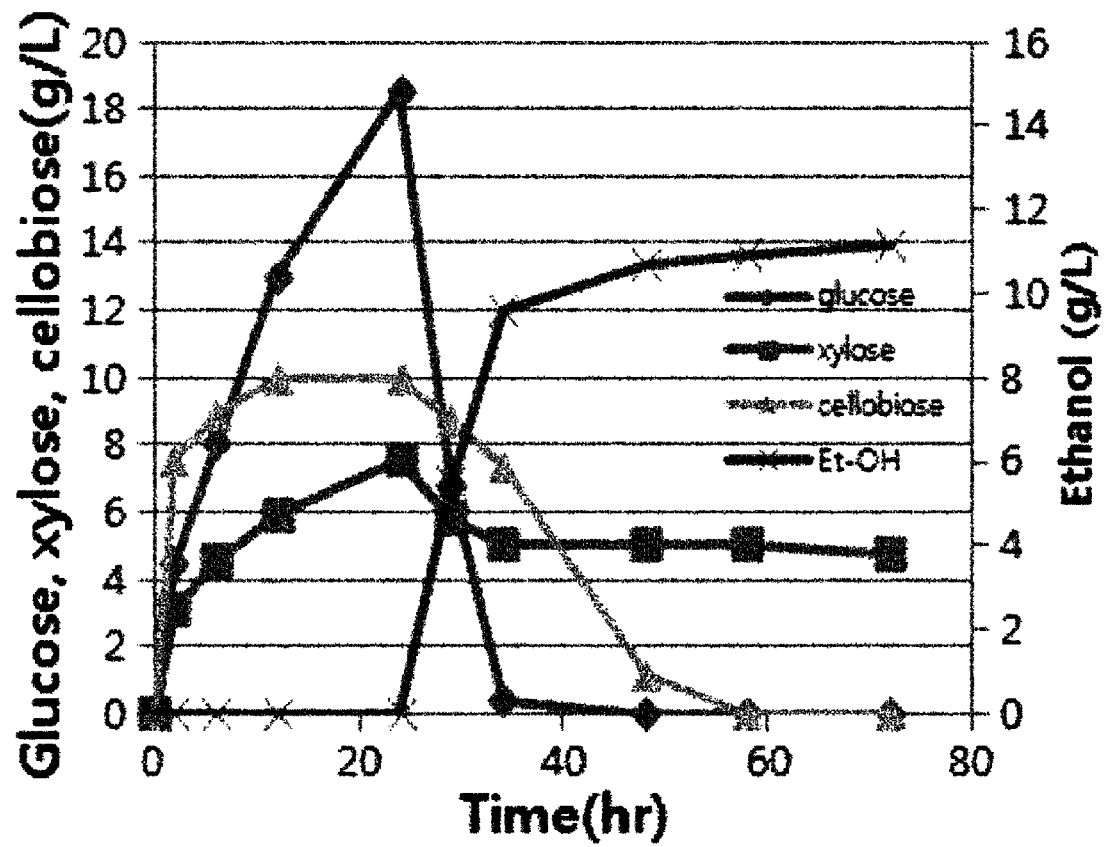
FIG. 16b is a graph showing changes in the cellobiose, xylose, glucose, and ethanol concentrations in the medium over cultivation time when ethanol was produced by culturing the control strain (Y2805Δgal80/YGaSW) introduced with only the vector in the medium containing Jerusalem artichokes tuber as a substrate under treatment of 5 FPU/g of cellulase.

FIG. 16b is a graph showing changes in the cellobiose, xylose, glucose, and ethanol concentrations in the medium over cultivation time when ethanol was produced by culturing the control strain (Y2805Δgal80/YGaSW) introduced with only the vector in the medium containing Jerusalem artichokes tuber as a substrate under treatment of 5 FPU/g of cellulase. As shown in FIG. 16b, the glucose, cellobiose and xylose concentrations increased after cultivation, but decreased after a predetermined time. When the glucose, cellobiose and xylose concentrations began to decrease, ethanol was produced. The ethanol concentration continuously increased, but was maintained at a predetermined level after a predetermined time. When the cultivation was completed, approximately 11 g/l of ethanol was produced.

As shown in FIGS. 16a and 16b, when the transformant (Y2805Δgal80/ST19-SfBGL1-10) introduced with the mutated beta-glucosidase gene provided by the present invention was used, ethanol productivity was increased to approximately 30% even though the cellulose-based agricultural biomass, Jerusalem artichokes tuber was used as a substrate.

Example 7-4-3: Production of Ethanol by Use of Gelidium Cellulose as Substrate

Figure 17A:
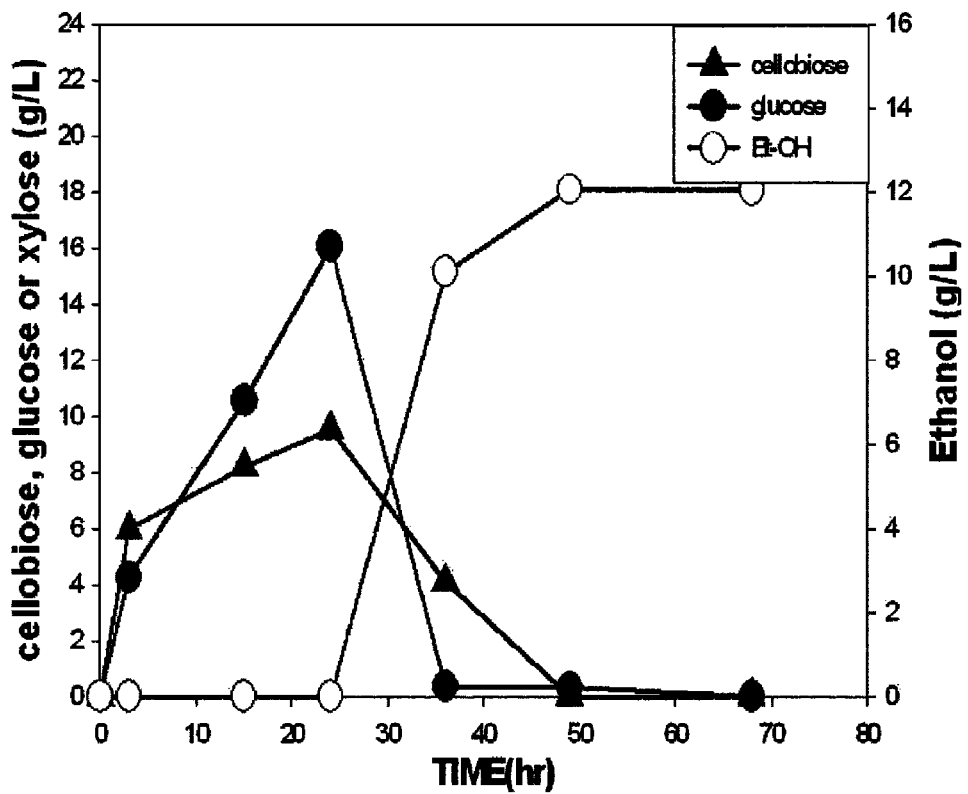
FIG. 17a is a graph showing changes in the cellobiose, glucose, and ethanol concentrations in the medium over cultivation time when ethanol was produced by culturing the transformant (Y2805Δgal80/ST19-SfBGL1-10) expressing the mutated beta-glucosidase in the medium containing 10% Gelidium cellulose as a substrate under treatment of 5 FPU/g of cellulase.
Figure 17B:
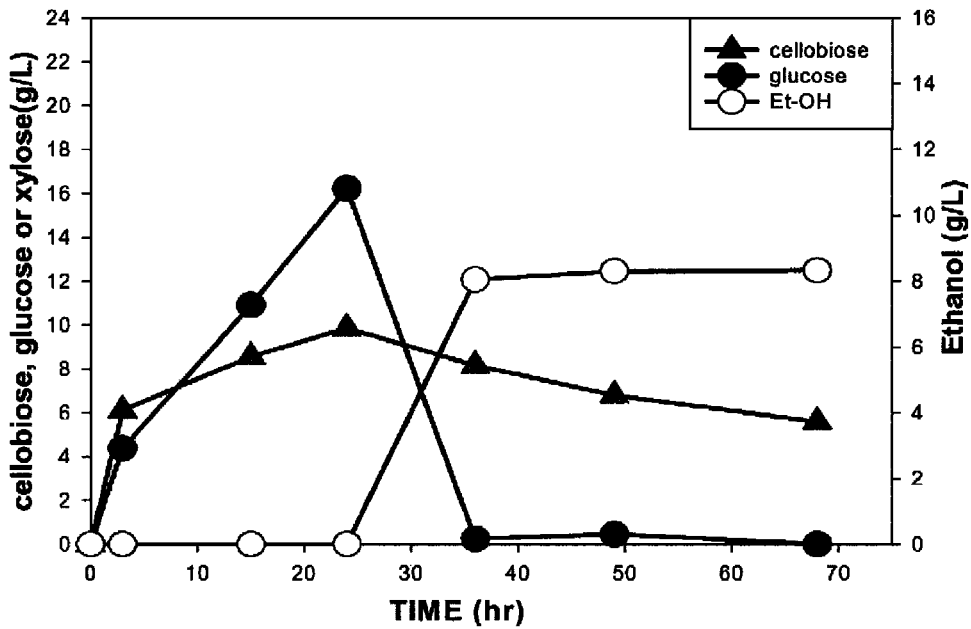
FIG. 17b is a graph showing changes in the cellobiose, glucose, and ethanol concentrations in the medium over cultivation time when ethanol was produced by culturing the control strain (Y2805Δgal80/YGaSW) introduced with only the vector in the medium containing 10% Gelidium cellulose as a substrate under treatment of 5 FPU/g of cellulase.

The experiment was performed in the same manner as in Example 7-4-1, except for using the seaweed-derived biomass Gelidium cellulose instead of palm fruit by-products (empty fruit bunch, EFB) (FIGS. 17a and 17b).

FIG. 17a is a graph showing changes in the cellobiose, glucose, and ethanol concentrations in the medium over cultivation time when ethanol was produced by culturing the transformant (Y2805Δgal80/ST19-SfBGL1-10) expressing the mutated beta-glucosidase in the medium containing 10% Gelidium cellulose as a substrate under treatment of 5 FPU/g of cellulase. As shown in FIG. 17a, the glucose and cellobiose concentrations increased after cultivation, but decreased after a predetermined time. When the glucose and cellobiose concentrations began to decrease, ethanol was produced. The ethanol concentration continuously increased, but was maintained at a predetermined level after a predetermined time. When the cultivation was completed, approximately 12 g/l of ethanol was produced.

FIG. 17b is a graph showing changes in the cellobiose, glucose, and ethanol concentrations in the medium over cultivation time when ethanol was produced by culturing the control strain (Y2805Δgal80/YGaSW) introduced with only the vector in the medium containing 10% Gelidium cellulose as a substrate under treatment of 5 FPU/g of cellulase. As shown in FIG. 17b, the glucose and cellobiose concentrations increased after cultivation, but the glucose concentration rapidly decreased and the cellobiose concentration slowly decreased after a predetermined time. When the glucose and cellobiose concentrations began to decrease, ethanol was produced. The ethanol concentration continuously increased, but was maintained at a predetermined level after a predetermined time. When the cultivation was completed, approximately 8 g/l of ethanol was produced.

As shown in FIGS. 17a and 17b, when the transformant (Y2805Δgal80/ST19-SfBGL1-10) introduced with the mutated beta-glucosidase gene provided by the present invention was used, ethanol productivity was increased to approximately 40% even though the seaweed-derived biomass, Gelidium cellulose was used as a substrate.

Effect of the Invention

Saccharification can be more efficiently performed by using the mutated beta-glucosidase of the present invention than the conventional beta-glucosidase, and thus it can be widely used for economic production of bioethanol.

What is claimed is:

1. A polynucleotide encoding a mutant beta-glucosidase polypeptide, wherein the mutant beta-glucosidase polypeptide has beta-glucosidase activity and comprises the amino acid sequence of SEQ ID NO: 10, except for: (a) a substitution of threonine (T) with alanine (A) at the amino acid corresponding to position 74 of SEQ ID NO: 10; and/or (b) a substitution of valine (V) with alanine (A) at the amino acid corresponding to position 275 of SEQ ID NO: 10.

2. The polynucleotide according to claim 1, wherein the amino acid sequence of the mutant beta-glucosidase polypeptide consists of the amino acid sequence SEQ ID NO: 12.

3. The polynucleotide according to claim 1, wherein the amino acid sequence of the mutant beta-glucosidase polypeptide consists of the amino acid sequence SEQ ID NO: 13.

4. The polynucleotide according to claim 1, wherein the mutant beta-glucosidase polypeptide comprises the amino acid sequence of SEQ ID NO: 10, except for: (a) the substitution of threonine (T) with alanine (A) at the amino acid corresponding to position 74 of SEQ ID NO: 10; and (b) the substitution of valine (V) with alanine (A) at the amino acid corresponding to position 275 of SEQ ID NO: 10.

5. A polynucleotide encoding a mutant beta-glucosidase polypeptide, wherein the encoded mutant beta-glucosidase polypeptide has beta-glucosidase activity, and wherein the polynucleotide consists of the nucleotide sequence of SEQ ID NO: 9.

6. A mutant beta-glucosidase polypeptide, wherein the mutant beta-glucosidase polypeptide has beta-glucosidase activity and comprises the amino acid sequence of SEQ ID NO: 10, except for: (a) a substitution of threonine (T) with alanine (A) at the amino acid corresponding to position 74 of SEQ ID NO: 10; and/or (b) a substitution of valine (V) with alanine (A) at the amino acid corresponding to position 275 of SEQ ID NO: 10.

7. An expression vector comprising the polynucleotide of claim 1.

8. The expression vector according to claim 7, further comprising a polynucleotide encoding a translational fusion partner (TFP).

9. An isolated host cell transformed with the expression vector of claim 7.

10. The host cell according to claim 9, wherein the host cell has an ethanol fermenting ability.

11. A method for producing a mutant beta-glucosidase polypeptide, comprising the steps of culturing the host cell of claim 9 in a culture medium to express the mutant beta-glucosidase encoded by the polynucleotide, and recovering the mutant beta-glucosidase polypeptide from the culture medium or culture supernatant thereof.

12. A method for producing bioethanol, comprising the steps of:
   (i) providing the host cell of claim 10;
   (ii) culturing the host cell in a culture medium containing a beta-glucosidase substrate to produce bioethanol; and
   (iii) recovering the bioethanol from the culture medium or culture supernatant thereof.

13. The method according to claim 12, wherein the host cell is a *Zymomonas* strain, a yeast strain or a *Bacillus* strain.

14. The method according to claim 12, wherein the beta-glucosidase substrate is a glucoside, an oligosaccharide or a biomass.

15. The method according to claim 12, wherein the beta-glucosidase substrate is one or more selected from the group consisting of maltose, trehalose, sucrose, turanose, lactose, cellobiose, maltotriose, raffinose, and kestose.

* * * * *